(12) United States Patent
Shin et al.

(10) Patent No.: US 9,999,403 B2
(45) Date of Patent: Jun. 19, 2018

(54) MEDICAL DEVICE

(71) Applicant: SAMSUNG MEDISON CO., LTD., Hongcheon-gun, Gangwon-do (KR)

(72) Inventors: Cheon Seop Shin, Seoul (KR); Soon Deok Kim, Uijeongbu-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 0 days. days.

(21) Appl. No.: 15/158,454

(22) Filed: May 18, 2016

(65) Prior Publication Data

US 2016/0338668 A1 Nov. 24, 2016

Related U.S. Application Data

(60) Provisional application No. 62/163,955, filed on May 19, 2015.

(30) Foreign Application Priority Data

Nov. 25, 2015 (KR) .................. 10-2015-0165305

(51) Int. Cl.
*F16M 11/00* (2006.01)
*A61B 8/00* (2006.01)
*F16H 21/44* (2006.01)
*F16M 11/08* (2006.01)
*F16M 11/24* (2006.01)
(Continued)

(52) U.S. Cl.
CPC .............. *A61B 8/4405* (2013.01); *A61B 8/00* (2013.01); *A61B 8/462* (2013.01); *A61B 8/467* (2013.01); *F16H 21/44* (2013.01); *F16M 11/045* (2013.01); *F16M 11/048* (2013.01); *F16M 11/08* (2013.01); *F16M 11/24* (2013.01);
(Continued)

(58) Field of Classification Search
USPC ........................................ 248/122.1
See application file for complete search history.

(56) References Cited

U.S. PATENT DOCUMENTS 5,924,988 A * 7/1999 Burris .................. A61B 8/00 600/437
6,510,049 B2 * 1/2003 Rosen .................. F16M 11/105 248/919

(Continued)

FOREIGN PATENT DOCUMENTS

JP 2001-353152 A 12/2001
KR 10-2015-0099229 A 8/2015

OTHER PUBLICATIONS

C. S. Shin "Ultrasound Control Panel Spin Arm Mechanism," Samsung Medison, Department of Institute/Design Group, May 22, 2015, pp. 1-14.

(Continued)

*Primary Examiner* — Monica E Millner
(74) *Attorney, Agent, or Firm* — McDermott Will & Emery LLP

(57) ABSTRACT

A medical device includes a body, a mobile unit connected to the body, a connection device configured to provide a movable connection between the body and the mobile unit to allow the mobile unit movable with respect to the body. The connection device includes a first rotator, a second rotator, a first connector, and a second connector. By the connection device, the mobile unit may be moved to a user desired position easily.

32 Claims, 23 Drawing Sheets

(51) Int. Cl.
*F16M 11/42* (2006.01)
*F16M 13/02* (2006.01)
*F16M 11/04* (2006.01)

(52) U.S. Cl.
CPC .......... *F16M 11/42* (2013.01); *F16M 13/022* (2013.01); *F16M 2200/08* (2013.01)

(56) References Cited

U.S. PATENT DOCUMENTS

| | | | |
|---|---|---|---|
| 6,648,289 B2* | 11/2003 | Toennesland | A61B 8/00 248/131 |
| 6,648,825 B1* | 11/2003 | Mesaros | A61B 8/00 600/437 |
| 6,709,391 B2* | 3/2004 | Mesaros | A61B 8/00 600/437 |
| 6,742,221 B2* | 6/2004 | Lu | G06F 1/162 16/366 |
| 8,333,698 B2* | 12/2012 | Ninomiya | A61B 8/00 600/407 |
| 9,380,997 B2* | 7/2016 | Nakajima | A61B 8/4405 |
| 9,451,931 B2* | 9/2016 | Ninomiya | B62B 3/02 |
| 9,597,057 B2* | 3/2017 | Ichimura | A61B 8/4427 |
| 2003/0025054 A1 | 2/2003 | Toennesland et al. | |
| 2003/0220571 A1 | 11/2003 | Mesaros et al. | |
| 2013/0030292 A1 | 1/2013 | Nakajima | |

OTHER PUBLICATIONS

Extended Search Report issued in corresponding European Patent Application No. 16170136.2, dated Sep. 30, 2016.

* cited by examiner

MEDICAL DEVICE

CROSS-REFERENCE TO RELATED APPLICATION(S)

This application claims the benefit of Korean Patent Application No. 10-2015-0165305, filed on Nov. 25, 2015 in the Korean Intellectual Property Office, and U.S. Provisional Patent Application No. 62/163,955 filled on May 19, 2015 in the United States Patent and Trademark office, the disclosures of which are incorporated herein by reference.

TECHNICAL FIELD

Embodiments of the present disclosure relate to a medical device to allow a mobile unit, which is movably connected to a body of the medical device, to be freely movable.

BACKGROUND

An ultrasonic imaging apparatus as an example of a medical device irradiates ultrasonic waves to a target part in an object through the surface of the object and noninvasively provides images about an examined part, such as a tomogram of a soft tissue or bloodstream, by using reflected ultrasonic waves that is echo ultrasonic waves.

An ultrasonic imaging apparatus is compact, inexpensive, and displaying a diagnostic imaging immediately as compared with another type of diagnostic imaging apparatus, e.g., X-ray device, Computerized Tomography (CT) scanner, Magnetic Resonance Image (MRI), diagnostic nuclear medical apparatus. In addition, the ultrasonic imaging apparatus is safe because there is no risk of radiation exposure. Therefore, the ultrasonic imaging apparatus is widely used in medical examination at maternity, cardiology, abdomen, and urology clinics.

The ultrasonic imaging apparatus includes a probe radiating ultrasonic waves and receiving reflected ultrasonic waves that is echo ultrasonic waves, a body controlling ultrasonic waves radiated through the probe and generating an image by using the received ultrasonic waves, and a control panel connected to the body to allow a user to operate the ultrasonic imaging apparatus.

The user operates the control panel in a state in which the probe makes contact with an object and the control panel is required to be moved to a convenient location for the operation of the user. At this time, moving a bulky body may not be easy and thus a structure configured to move the control panel, which is independently moved from the body and to meet the needs of the user, may be needed.

SUMMARY

Therefore, it is an aspect of the present disclosure to provide a medical device including a mobile unit movably installed according to the needs of a user.

It is another aspect of the present disclosure to provide a medical device capable of moving a mobile unit to a position that is desired by a user, and fixing the mobile unit to the position.

Additional aspects of the present disclosure will be set forth in part in the description which follows and, in part, will be obvious from the description, or may be learned by practice of the invention.

In accordance with one aspect of the present disclosure, a medical device includes a body, a mobile unit movably connected to the body, and a connection device configured to provide a movable connection between the body and the mobile unit. The connection device may include a first rotator and a second rotator both of which are rotatably connected to each other, a first connector pivotally connected to the first rotator, and a second connector pivotally connected to the second rotator.

The first rotator and the second rotator may be rotatably connected to the body and the first connector and the second connector may be pivotally connected to the mobile unit.

The first rotator and the second rotator may be formed in a disk shape having the same radius. The first connector may be pivotally connected an outer circumference of the first rotator and the second connector may be pivotally connected an outer circumference of the second rotator.

The first connector and the second connector may have a curved shape to surround an outer circumference of the first rotator and the second rotator.

The connection device may further include a rotation control member configured to limit a rotation angle of the first rotator and the second rotator. A rotatable area of a first hinge, in which the first rotator and the first connector are connected to each other, and a second hinge, in which the second rotator and the second connector are connected to each other, may be limited through the rotation control member.

A rotatable angle area of the first rotator and the second rotator, which is limited by the rotation control member, may be bilaterally symmetrical about a rotation shaft.

The connection device may further include a first controller configured to control a rotation of the first rotator and the second rotator.

The connection device may further include a second controller configured to control a pivot of the first connector and the second connector.

The first rotator and the second rotator may be rotatably connected to the mobile unit, and the first connector and the second connector may be rotatably connected to the body.

In accordance with another aspect of the present disclosure, a medical device includes a body, a mobile unit movably connected to the body, and a connection device configured to provide a movable connection between the body and the mobile unit. The connection device may include a first hinge and a second hinge both of which are rotated about a rotation shaft, a third hinge rotated about the first hinge, and a fourth hinge rotated about the second hinge.

The rotation shaft may be connected to the body, and the third hinge and the fourth hinge may be connected to the mobile unit.

The connection device may further include a rotation control member configured to limit a rotation angle of the first hinge and the second hinge.

The first hinge and the second hinge may have the same rotation radius, and a rotatable angle area of the first hinge and the second hinge may be bilaterally symmetrical about the rotation shaft.

The connection device may further include a first controller configured to control a rotation of the first hinge and the second hinge about the rotation shaft.

The connection device may further include a second controller configured to control a rotation of one or more of the first hinge and the third hinge, and one or more of the second hinge and the fourth hinge.

The rotation shaft may be connected to the mobile unit, and the third hinge and the fourth hinge may be connected to the body.

In accordance with another aspect of the present disclosure, a medical device includes a body, a mobile unit movably connected to the body, and a connection device configured to provide a movable connection between the body and the mobile unit. The connection device may include a first rotator and a second rotator both of which are rotatably coupled to a rotation shaft, which is provided in a base, and formed in a disk shape having the same radius, a first connector whose one end portion is pivotally connected to an outer circumference of the first rotator, and a second connector whose one end portion is pivotally connected to an outer circumference of the second rotator.

The base may be fixed to the body, and the other end portion of the first connector and the other end portion of the second connector may be pivotally connected to the mobile unit.

The connection device may further include a rotation control member configured to limit a rotation angle of the first rotator and the second rotator. The rotation control member may be formed in a position spaced apart from the rotation shaft with a certain distance to have a pillar shape so as to penetrate the first rotator and the second rotator. The first rotator and the second rotator may respectively include a guide slit formed in an arc shape to guide a rotation area limited by the rotation control member and to allow the rotation control member to penetrate thereto.

The connection device may further include a cap non-rotatably coupled to the other end of the rotation shaft whose one end is fixed to a base, wherein the opposite ends of the rotation control member may be fixed to the base and the cap.

The guide slit of the first rotator and the guide slit of the second rotator may be provided symmetrically about the rotation shaft so that a rotatable angle area of the first rotator and the second rotator may be symmetrical about the rotation shaft.

The first connector and the second connector may have a curved shape in a state of being folded so as to surround an outer circumference of the first rotator and the second rotator in a position of being folded.

The connection device may further include a first controller configured to control a rotation of the first rotator and the second rotator, and a second controller configured to control a pivot of the first connector and the second connector.

The base may be rotatably fixed to the body or the mobile unit so that the connection device may be pivoted against the body.

The medical device may further include a controller configured to control a rotation of the base.

The medical device may further include a lifting device disposed between the base and the body so that the mobile unit is moved up and down.

The based may be fixed to the mobile unit and the other end portion of the first connector and the other end portion of the second connector may be pivotally connected to the body.

In accordance with another aspect of the present disclosure, a medical device includes a body, a mobile unit movably connected to the body, a first connector provided with a first connection part rotatably coupled to the body and a second connection part rotatably coupled to the mobile unit, a second connector provided with a third connection part rotatably coupled to the body and a fourth connection part rotatably coupled to the mobile unit, a guide rail installed on the body or the mobile unit to allow the first connection part and the third connection part or the second connection part and the fourth connection part to be moved in a slide manner, and a link having a variable length and configured to connect the first connection part and the third connection part or to connect the second connection part and the fourth connection part moved in the guide rail in the slide manner.

The guide rail may include a first rail in which the first connection part or the second connection part is moved in the slide manner and a second rail in which the third connection part or the fourth connection part is moved in the slide manner. The first rail and the second rail may have an arc shape having the same curvature radius, the same center of curvature and being bilaterally symmetrical.

In accordance with another aspect of the present disclosure, a medical device includes a body, a mobile unit movably connected to the body, a first connector provided with a first connection part rotatably coupled to the body and a second connection part rotatably coupled to the mobile unit, a second connector provided with a third connection part rotatably coupled to the body and a fourth connection part rotatably coupled to the mobile unit, a base rotatably coupled to the body or the mobile unit, and a guide rail installed on the base to allow the first connection part and the third connection part or the second connection part and the fourth connection part to be moved in a slide manner.

The medical device may further include a link having a variable length and configured to connect the first connection part and the third connection part or to connect the second connection part and the fourth connection part moved in the guide rail in the slide manner.

The base may have a disk shape and the guide rail may be formed in an upper surface or a lateral surface of the base.

In accordance with another aspect of the present disclosure, a medical device includes a body, a mobile unit movably connected to the body, and a connection device configured to provide a movable connection between the body and the mobile unit. The connection device may include a base coupled to the body or the mobile unit, a guide rail installed on the base, a first rotator and a second rotator moved in the guide rail in a slide manner, a first connector pivotally connected to the first rotator, and a second connector pivotally connected to the second rotator.

The base may have a disk shape and the guide rail may be formed in a circular shape having the same center of curvature as the base.

The first rotator may include a first rotation part accommodated and rotated in the guide rail and a first hinge connected to the first connector, and the second rotator may include a second rotation part accommodated and rotated in the guide rail and a second hinge connected to the second connector.

The first connector may include a first connection part rotatably coupled to the first rotator and a second connection part rotatably coupled to the body or the mobile unit to which the base is not coupled, and the second connector may include a third connection part rotatably coupled to the second rotator and a fourth connection part rotatably coupled to the body or the mobile unit to which the base is not coupled.

A bearing ball may be accommodated in the first rotation part and the second rotation part.

In accordance with another aspect of the present disclosure, a medical device includes a body, a mobile unit, and a connection device connecting the body and the mobile unit to each other. The connection device includes a first connector having first and third ends respectively connected to the body and the mobile unit and rotatable around each other, and a second connector having second and fourth ends respectively connected to the body and the mobile unit and rotatable around each other. Two ends selected from a first pair of ends including the first end of the first connector and the third end of the second connector and a second pair of ends including the third end of the first connector and the fourth end of the second connector, are respectively rotatable along first and second concentric paths in one of the body and mobile unit. The other two ends selected from the first and second pairs are pivotally connected to the other one of the body and mobile unit.

The medical device further includes a rotation shaft and first and second rotators rotatable around the rotation shaft. Centers of the first and second rotators are penetrated by the rotation shaft. The first end of the first connector is connected to an edge of the first rotator and the second end of the second connector is connected to an edge of the second rotator.

The first and second concentric paths are respectively determined by first and second guide rails in the one of the body and mobile unit. The first end of the first connector and the second end of the second connector are connected by a length adjustable link, and are slidable along the first and second guide rails, respectively.

The medical device further includes a base including first and second guide rails and rotatable around a rotation shaft located at a center of the base. The first end of the first connector and the second end of the second connector are connected by a length adjustable link, and are slidable along the first and second guide rails, respectively.

The medical device further includes a base including first and second guide rails. The first end of the first connector and the second end of the second connector are respectively coupled to the first and second guide rails by first and second bearings which are slidable in the first and second guide rails.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
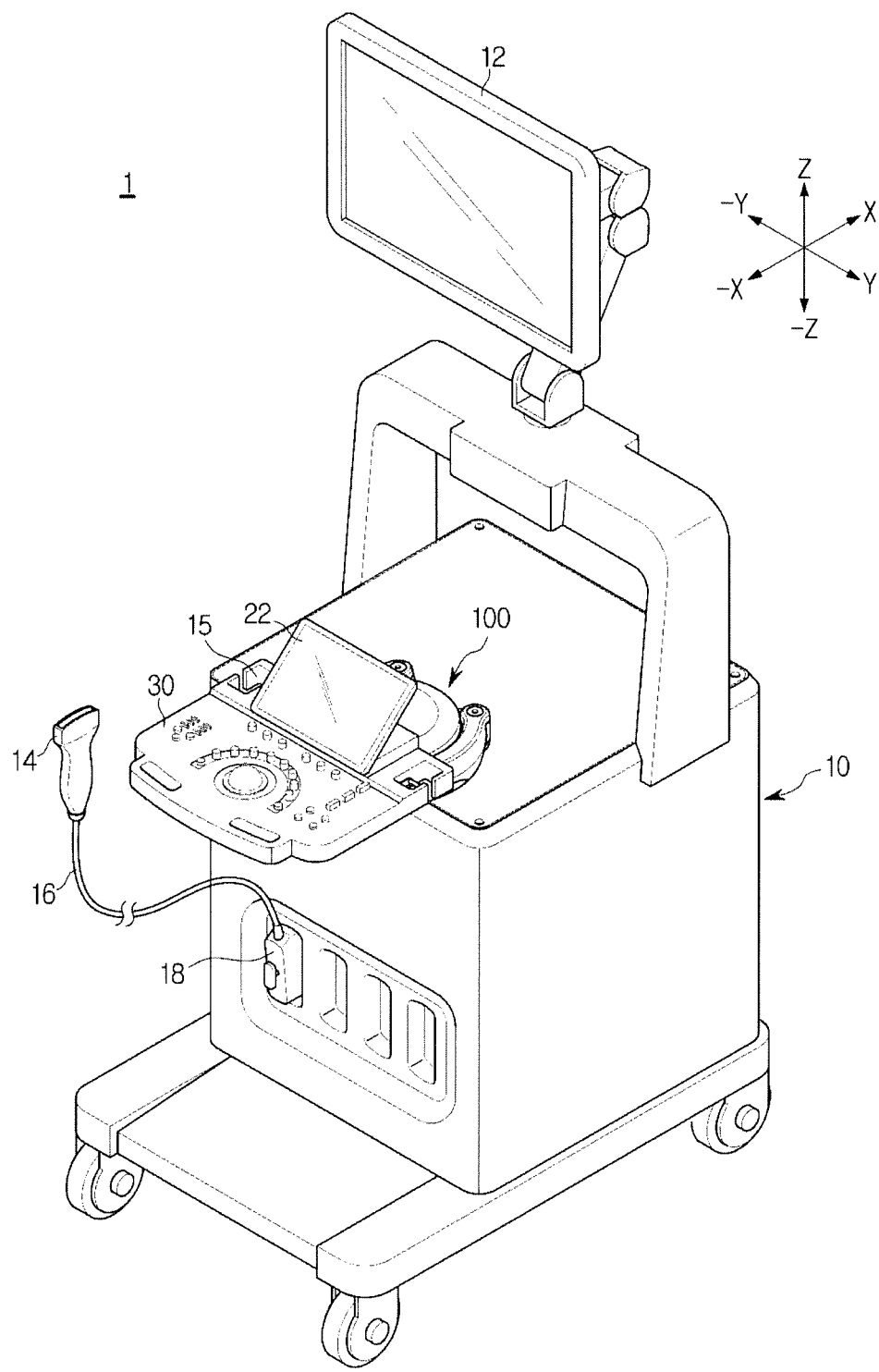
FIG. 1 is a perspective view illustrating a medical device according to an embodiment of the present disclosure.

The present disclosure will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Parts which are not associated with the description are omitted in order to specifically describe the present disclosure, and like reference numerals refer to like elements throughout the specification Also, terms used herein are used to described embodiments, and thus there is no intention to limit/or restrict the present invention. Expression in the singular should be understood to include multiple representations unless it represents clearly different meaning in the context. Terms such as "comprising", "providing" or "having" are intended to designate the presence of features, numbers, steps, operations, elements, or components or a combination thereof, but it does not preclude the presence or addition of a part or a combination of these things.

It will be understood that, although the terms first, second, third, etc., may be used herein to describe various elements, but elements are not limited by these terms. These terms are only used to distinguish one element from another element. For example, without departing from the scope of the present disclosure, a first element may be termed as a second element, and a second element may be termed as a first element. The term of "and/or" includes a plurality of combinations of relevant items or any one item among a plurality of relevant items.

An ultrasonic imaging apparatus as an example of a medical device according to an embodiment of the present disclosure will be described with reference to accompanying drawings.

Figure 2:
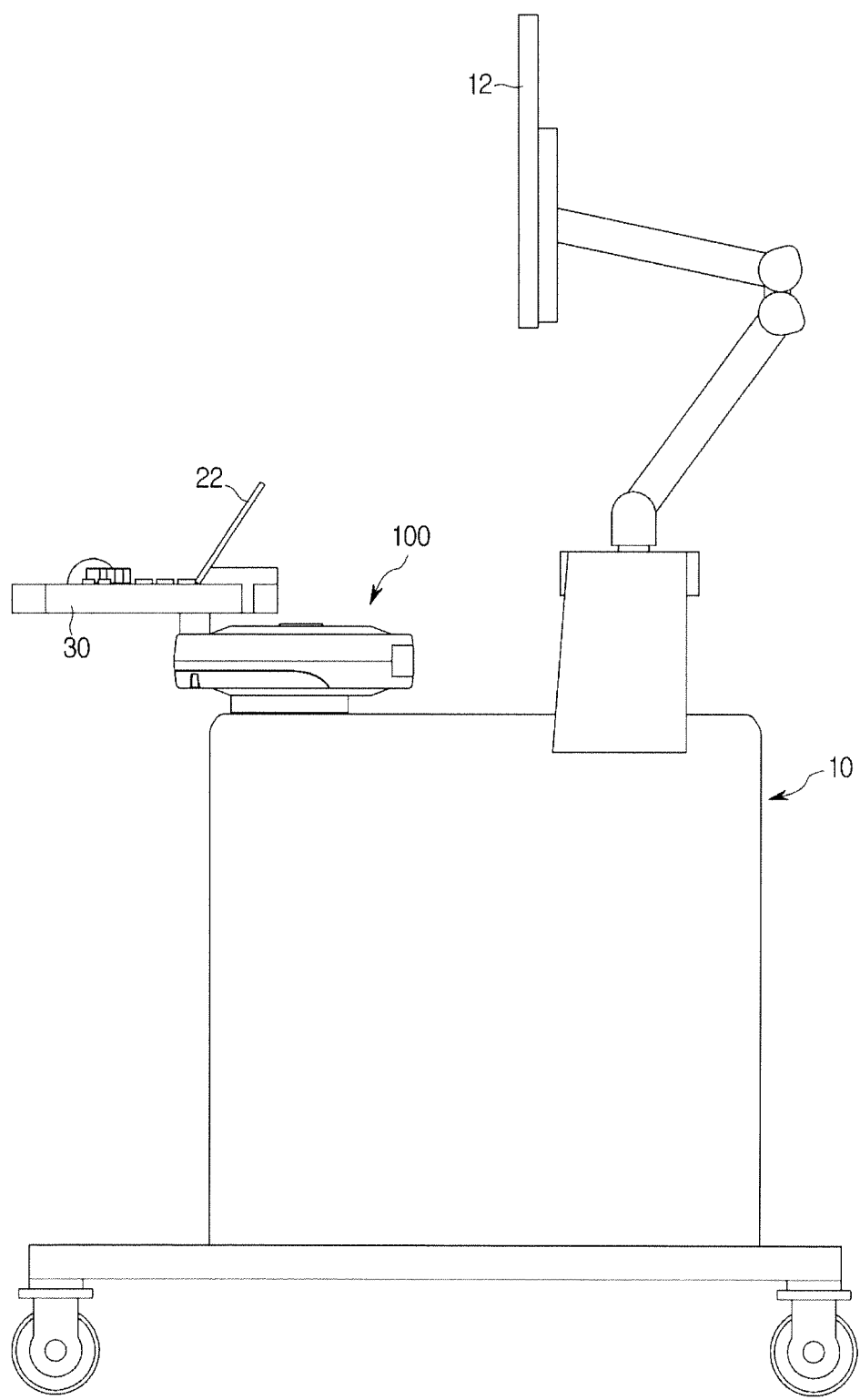
FIG. 2 is a lateral view illustrating the medical device of FIG. 1.

FIG. 1 is a perspective view illustrating a medical device according to an embodiment of the present disclosure and FIG. 2 is a lateral view illustrating the medical device of FIG. 1.

A medical device 1 such as an ultrasonic image apparatus may include a body 10, a display 12 disposed on the body 10, a probe 14, and a control panel 30.

The display 12 and the control panel 30 may be movably connected to one side of the body 10. In addition to the display 12 and the control 30, other devices of the medical device 1 may be movably connected to one side of the body 10. The devices movably connected to the body 10 may be referred to as "mobile unit". A description thereof will be described later.

In the body 10, a variety of components, e.g. a Central Processing Unit (CPU), a Micro Control Unit (MCU), and an image signal processor configured to control transmission of ultrasonic signal or configured to process the received ultrasonic signal, may be equipped.

The display 12 may be installed on an upper portion of the body 10 to display a result of the ultrasonic diagnosis as an image. The display 12 may be mounted to the body 10 as illustrated in FIG. 1, and alternatively mounted to the control panel 30.

The display 12 may display an ultrasound image according to a pre-determined display mode or a display mode set by a user. The display mode may include an Amplitude mode (A-mode), a Brightness mode (B-mode), a Doppler mode (D-mode), an Elastography mode (E-mode), and a Motion mode (M-mode).

The display 12 may be implemented by Liquid Crystal Display (LCD), Light Emitting Diode (LED), Organic Light Emitting Diode (OLED), Plasma Display Panel (PDP), or Cathode-Ray Tube (CRT).

The probe 14 may include a plurality of transducers. The transducer may convert an ultrasonic signal into an electrical signal and vice versa, transmit the ultrasonic signal to an object, and receive an echo ultrasonic signal reflected from the object.

According to a working principle of inter-converting an ultrasonic signal into an electrical signal, the transducer may be a Magnetostrictive Ultrasound Transducer (MUT) that uses magnetostrictive effects of a magnetic substance, a Capacitive Micromachined Ultrasonic Transducer (cMUT) that uses vibration of hundreds or thousands of microfabricated thin films, or a Piezoelectric Ultrasonic Transducer (PUT) that uses piezoelectric effects of a piezoelectric substance.

The probe 14 may be connected to the body 10 through a cable 16. One end of the cable 16 may be connected to the probe 14, and the other end of the cable 16 may be connected to a male connector 18. The male connector 18 may be physically coupled to a female connector (not shown) provided in the body 10 so that the probe 14 may be connected to the body 10.

FIG. 1 illustrates that the male connector 18 and the cable 16 are exposed to the outside, but alternatively the male connector 18 and the cable 16 may be equipped in a housing forming the body 10. FIG. 1 illustrates that a probe holder 15 on which the probe 14 can be hung up, is provided in the control panel 30, but alternatively, the probe holder 15 may be provided in the body 10 for the user convenience. In addition, the probe holder 15 may be provided in both of the body 10 and the control panel 30.

The control panel 30 may allow a user to control the medical device 1. In the control panel 30, an input device, and a sub-display 22 may be provided. The input device may include a variety of buttons including a move button, a knob, a trackball, and a joy stick. The sub-display 22 may provide information related to a menu to optimize an ultrasound image or a secondary image, or a graphic interface to a user.

Similar to the display 12, the sub-display 22 may be implemented by Liquid Crystal Display (LCD), Light Emitting Diode (LED), Organic Light Emitting Diode (OLED), Plasma Display Panel (PDP), or Cathode-Ray Tube (CRT). In addition, the sub-display 22 may be implemented by a touch screen with a touch panel.

As mentioned above, the medical device 1 may include a mobile unit movably connected to one side of the body 10. A user needs to perform a scanning besides a patient for a long time for the ultrasound diagnosis, and in addition, the user needs to operate a variety of devices, e.g. a mobile device while scanning. Therefore, for the user convenience, the medical device 1 may provide a structure configured to allow the mobile unit to be freely movable according to the user intension while the mobile unit is connected to the body 10.

Particularly, the user may mainly move the control panel 30 controlling the operation of the medical device 1. Hereinafter an embodiment of the present disclosure will be described with the control panel 30 as an example of the mobile unit.

Therefore, the medical device 1 may include a connection device 100 configured to movably connect the control panel 30 to the body 10.

In embodiments of the present disclosure, with respect to a position of the body 10, a front side may represent an X axis direction, a rear side may represent an −X axis direction, a right side may represent a Y axis direction, a left side may represent a −Y axis direction, an upper side may represent a Z axis direction, and a lower side may represent a −Z axis direction. Hereinafter the X axis and the −X axis may represent a direction in which the control panel 30 is reciprocally moved forward to and backward from the body 10.

Hereinafter the shape and the structure of the connection device 100 will be described.

Figure 3:
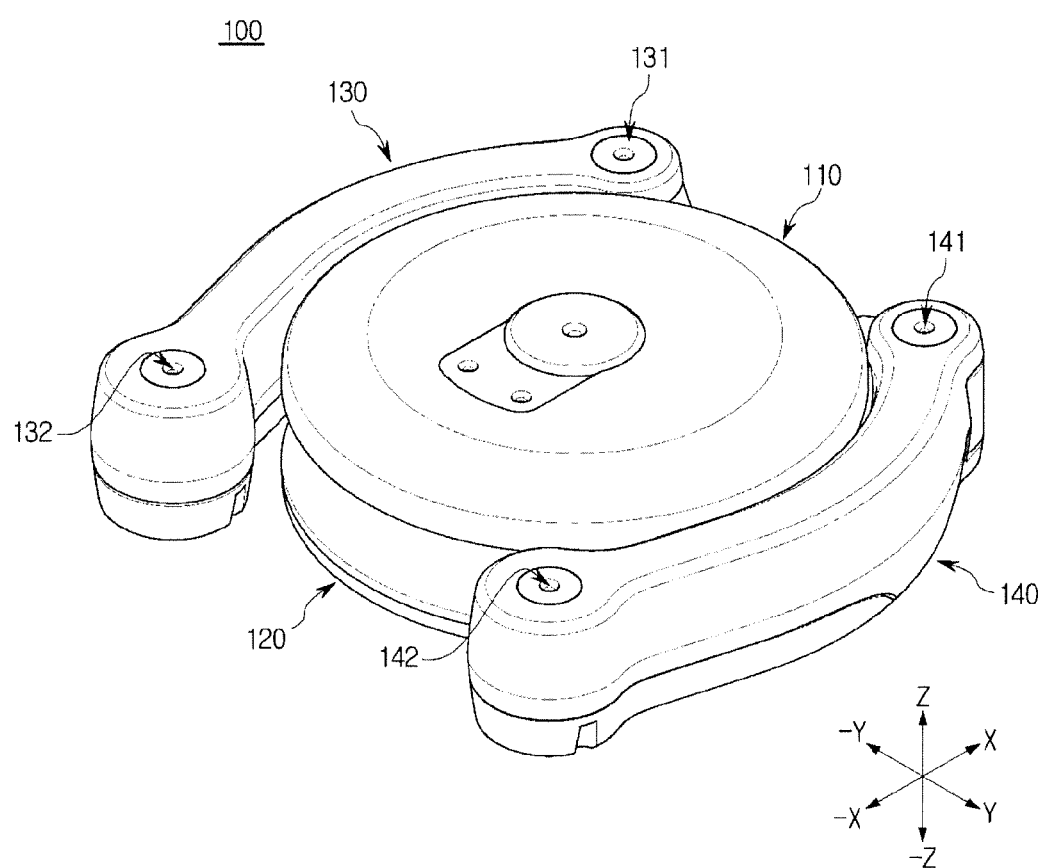
FIG. 3 is a perspective view illustrating a connection device connecting a body to a mobile unit of the medical device of FIG. 1.
Figure 4:
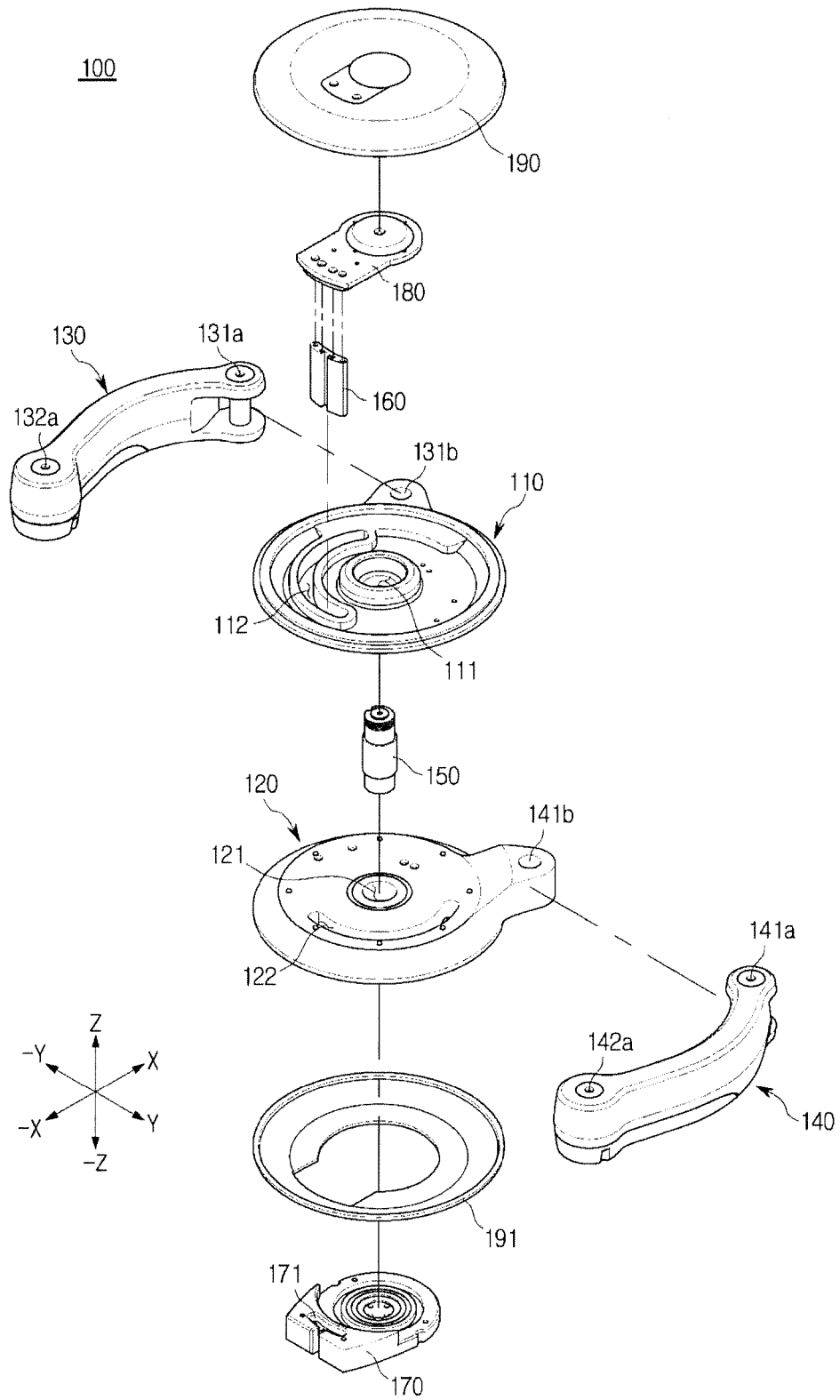
FIG. 4 is an exploded perspective view illustrating the connection device of FIG. 3.

FIG. 3 is a perspective view illustrating a connection device connecting a body to a mobile unit of the medical device of FIG. 1 and FIG. 4 is an exploded perspective view illustrating the connection device of FIG. 3.

Referring to FIGS. 3 and 4, the connection device 100 of the medical device 1 according to an embodiment of the present disclosure, may include a first rotator 110, and a second rotator 120 both of which are rotatably connected to each other, and further include a first connector 130 pivotally connected to the first rotator 110, and a second connector 140 pivotally connected to the second rotator 120.

The first rotator 110 and the second rotator 120 may have any shape, but may have approximately a disc shape. In addition, the first rotator 110 and the second rotator 120 may respectively include a penetration hole 111 and 121 which a rotation shaft 150 penetrates through. The first rotator 110 and the second rotator 120 may be vertically coupled to the same rotation shaft 150 so as to be rotated with respect to the same center of rotation.

Although not shown in the drawings, by appropriate design changes, the first rotator and the second rotator is not disposed vertically and it may also be arranged on the same plane.

The rotation shaft 150 may be directly connected to the body 10, or the rotation shaft 150 may be coupled to the body 10 in a way that the rotation shaft 150 is coupled to a base 170 and then the base 170 is coupled to the body. Therefore, the first rotator 110 and the second rotator 120 may be rotatably connected to the body 10, or the first rotator 110 and the second rotator 120 may be rotatably connected to the base 170 of the connection device 100.

The first connector 130 and the second connector 140 may have any shape, but may have a shape corresponding to the shape of the first rotator 110 and the second rotator 120. That is, the first connector 130 and the second connector 140 may have a curved shape to surround an outer circumference of the first rotator 110 and the second rotator 120 at a position adjacent to the first rotator 110 and the second rotator 120.

Opposite end portions of the first connector 130 and the second connector 140 may each have a hinge structure so that the opposite end portions of the first connector 130 are pivotally connected to the first rotator 110 and the control panel 30, respectively, through the hinge structures. Similarly, opposite end portions of the second connector 140 are pivotally connected to the second rotator 120 and the control panel 30, respectively, through hinge structures thereof.

One end portion of the first connector 130 that is a connection part between the first connector 130 and the first rotator 110 may represent a first hinge 131, and one end portion of the second connector 140 that is a connection part between the second connector 140 and the second rotator 120, may represent a second hinge 141. In addition, the other end portion of the first connector 130 that is a connection part between the first connector 130 and the control panel 30 may represent a third hinge 132 and the other end portion of the second connector 140 that is a connection part between the second connector 140 and the control panel 30 may represent a fourth hinge 142.

To illustrate with respect to the hinge, the first hinge 131 and the second hinge 141 may be rotatable about the rotation shaft 150, the third hinge 132 may be rotatable about the first hinge 131, and the fourth hinge 142 may be rotatable about the second hinge 141. The first rotator 110 may connect the rotation shaft 150 to the first hinge 131, the second rotator 120 may connect the rotation shaft 150 to the second hinge 141, the first connector 130 may connect the first hinge 131 to the third hinge 132, and the second connector 140 may connect the second hinge 141 to the fourth hinge 142.

Particularly, a first hinge hole 131*b*, to which a first hinge pin 131*a* of the first connector 130 is pivotally connected, may be provided in the outer circumference of the first rotator 110 formed in a disk shape, and a second hinge hole 141*b*, to which a second hinge pin 141*a* of the first connector 130 is pivotally connected, may be provided in the outer circumference of the second rotator 120 formed in a disk shape. In addition, a third hinge pin 132*a* and a fourth hinge pin 142*a* may be respectively provided in the other end portions of the first connector 130 and the second connector 140 to be pivotally coupled to the control panel 30.

As mentioned above, when the first connector 130 and the second connector 140 are formed in the curved shape to correspond to the disk shape of the first rotator 110 and the second rotator 120, through the first connector 130 and the second connector 140, a direction of a force applied to the first hinge 131 and the second hinge 141 may coincide with a direction of a force to rotate the first rotator 110 and the second rotator 120 that is the tangential direction of the disk, and thus it may be advantageous in the transmission of the force. Therefore, an external force for the movement of the control panel 30 may be easily delivered to the first rotator 110 and the second rotator 120 through the first connector 130 and the second connector 140 so that the control panel 30 may be moved in an easier manner.

Referring to FIGS. 1 and 2, the connection device 100 may be disposed in a way that the first rotator 110 and the second rotator 120 are rotatably connected to the body 10 and the third hinge 132 of the first connector 130 and the fourth hinge 142 of the second connector 140 are pivotally connected to the control panel 30, as mentioned above.

Although not shown in the drawings, the connection device 100 may be disposed in a way that the first rotator 110 and the second rotator 120 are rotatably connected to the control panel 30 and the third hinge 132 of the first connector 130 and the fourth hinge 142 of the second connector 140 are pivotally connected to the body 10.

Referring to FIGS. 3 and 4, the connection device 100 may further include a rotation control member 160 configured to limit a rotation angle of the first rotator 110 and the second rotator 120. The rotation angle of the first rotator 110 and the second rotator 120 may be limited by the rotation control member 160 so that a rotatable area of the first hinge 131 and the second hinge 141, both of which are rotated to have the same radius of rotation about the rotation shaft 150, may be limited.

When the rotatable area of the first hinge 131 and the second hinge 141 are limited, the collision between the first hinge 131 and the second hinge 141 caused by the rotation may be prevented. The rotation angle limited by the rotation control member 160 may be determined to secure a sufficient area to allow the control panel 30 to move forward, backward, left and right with respect to the body 10 and to maintain the rigidity of the connection device 100.

The rotatable area of the first rotator 110 and the second rotator 120 limited by the rotation control member 160 may be limited to be bilaterally symmetrical about the rotation shaft 150 so that an area in which the control panel 30 is movable is bilaterally symmetrical. In other words, a rotatable area of the first hinge 131 and the second hinge 141 may be limited to be bilaterally symmetrical about the rotation shaft 150.

As illustrated in FIG. 4, the rotation control member 160 may have a pillar shape to penetrate the first rotator 110 and the second rotator 120 at a position spaced apart from the rotation shaft 150 with a certain distance.

The first rotator 110 and the second rotator 120 may respectively include a guide slit 112 and 122 formed in an arc shape to allow the rotation control member 160 to be penetrated thereto, and configured to guide the rotation area limited by the rotation control member 160.

A first guide slit 112 provided in the first rotator 110 and a second guide slit 122 provided in the second rotator 120 may be formed symmetrically about the rotation shaft 150 so that the rotatable area of the first rotator 110 and the second rotator 120 may be symmetrical about the rotation shaft 150.

The rotation control member 160 may be formed in a cylindrical shape or a pillar shape having a cross-sectional area thereof being an arc to correspond to the curvature of the guide slit 112 and 122 to have a sufficient rigidity.

As illustrated in FIG. 4, when the connection device 100 includes the base 170, one end portion of the rotation control member 160 may be fixed to an accommodation groove 171 provided in the base 170. Alternatively, although not shown, one end portion of the rotation control member 160 may be directly fixed to the body 10 when the connection device 100 does not include the base 170 and the rotation shaft 150 is directly fixed to the body 10.

In addition, the connection device 100 may further include a cap 180 configured to fix the other end portion of the rotation control member 160 and the rotation shaft 150 from an upper portion. By the cap 180, the rigidity of the rotation shaft 150 and the rotation control member 160 may be improved.

The connection device 100 may further include an upper cover 190 covering an upper surface of the first rotator 110 and a lower cover 191 covering a lower surface of the second rotator 120. By the upper cover 190 and the lower 191, the rotation shaft 150, the rotation control member 160 and the guide slit 112 and 122 may be protected so that a foreign material, e.g. dust is not introduced thereto, and a beautiful appearance may be realized.

In addition, the connection device 100 may further include a first controller 114 (see FIG. 5) controlling the rotation of the first rotator 110 and the second rotator 120 and a second controller 144 (see FIG. 5) controlling the pivot of the first connector 130 and the second connector 140.

To illustrate with respect to the hinge, the connection device 100 may further include a first controller 114 controlling the rotation of the first hinge 131 and the second hinge 141 about the rotation shaft 150 and a second controller 144 controlling the rotation of at least one of the first hinge 131 and the third hinge 132 and at least one of the second hinge 141 and the fourth hinge 142.

Figure 5:
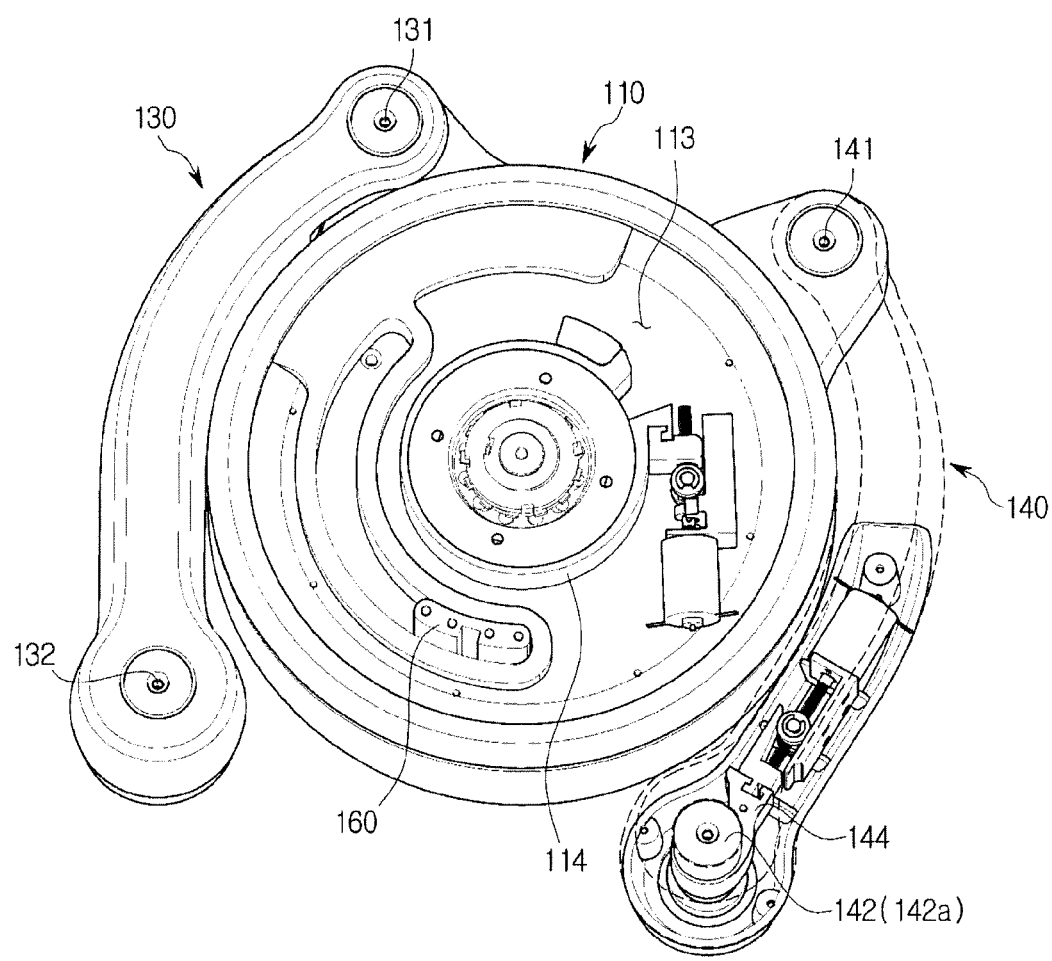
FIG. 5 is a view illustrating a controller of the connection device of the medical device of FIG. 1.

FIG. 4 illustrates the connection device 100 in which the first controller 114 is omitted, but FIG. 5 illustrates a control unit of a connection device of a medical device according to an embodiment of the present disclosure.

FIG. 5 illustrates the connection device 100 in which the upper cover 190 and the cap 180 are removed to expose the first control unit 114 and illustrates a perspective view of the second connection unit 140 to expose the second control unit 144.

Referring to FIGS. 4 and 5, the first rotator 110 may include an accommodation unit 113 recessed on an upper surface to accommodate the first controller 114. In addition, an inner space of the second connector 140 may accommodate the second controller 144.

Although FIG. 5 illustrates only the first controller 114 configured to control the rotation of the first rotator 110, another first controller for the control of the second rotator 120 may be mounted to an accommodation unit provided in a lower surface of the second rotator 120 since the second rotator 120 may be formed to have a symmetrical shape vertically and horizontally with respect to the first rotator 110.

In addition, although FIG. 5 illustrates only the second controller 144 configured control the pivot of the second connector 140, another second controller 144 may be accommodated in an inner space of the first connector 130 to control the pivot of the first connection unit 130.

The second controller 144 may control the pivot movement of the first hinge 131 and the second hinge 141 and/or the third hinge 132 and the fourth hinge 142 to control the pivot movement of the first connector 130 and the second connector 140.

According to an embodiment illustrated in FIGS. 3 to 5, the first hinge pin 131a and the second hinge pin 141a may be non-rotatably fixed to the first connector 130 and the second connector 140, respectively and the third hinge pin 132a and the fourth hinge pin 142a may be non-rotatably fixed to the control panel 30, and thus the second controller 144 may be disposed to control the pivot of the third hinge 132 and the fourth hinge 142.

Although not shown, according to design changes, the second controller 144 may be mounted to the first rotator 110 and the second rotator 120 to control the pivot movement of the first hinge 131 and the second hinge 141, and according to the change of the hinge structure of the first hinge to the fourth hinge 131, 132, 141, and 142, the position of the second controller 144 may be changed.

A movement of the control panel 30 will be described later, and the rotatable angle area of the first rotator 110 and the second rotator 120 limited by the rotation control member 160 may be bilaterally symmetrical about the rotation shaft 150 so that a movable area of the control panel 30 becomes symmetrical.

In a state in which the base is not included in the connection device 100, when the rotation shaft 150 and the rotation control member 160 are directly fixed to the body 10, the movable area of the control panel 30 may become bilateral symmetry about the body 10. In addition, in a state in which the base 170 is included in the connection device 100, when the base 170 is non-rotatably fixed to the body 10, the control panel 30 may be moved bilaterally symmetrical about the body 10.

Although not shown in the drawings, the base 170 may be rotatably connected to the body 10. Accordingly, since the connection device 100 is pivoted about the body 10, the control panel 30 may perform a rotation movement about the body 10 regardless of the movable area of the control panel 30 determined by the rotation control member 160. The rotation center of the base 170 against the body 10 may be configured to be concentric with the rotation shaft 150 of the connection device 100.

In addition, when the base 170 is rotatably connected to the body 10, the medical device according an embodiment may further include a separate controller configured to control the rotation of the base 170. The separate controller configured to control the rotation of the base 170 may fix the connection device 100 to be rotated against the body 10 and in accordance with the user convenience, a user may adjust the movable area of the control panel 30 by the connection device 100, rather than the bilateral symmetry about the body 10, the through an operation of the controller.

Although not shown in the drawings, the medical device according to an embodiment may further include a lifting device between the base 170 of the connection device 100 and the body 10 to allow the control panel 30 to be moved vertically.

Hereinafter an operation of the control panel 30, which is performed through a structure of the connection device 100 connecting the control panel 30 to the body 10, will be described.

Figure 6:
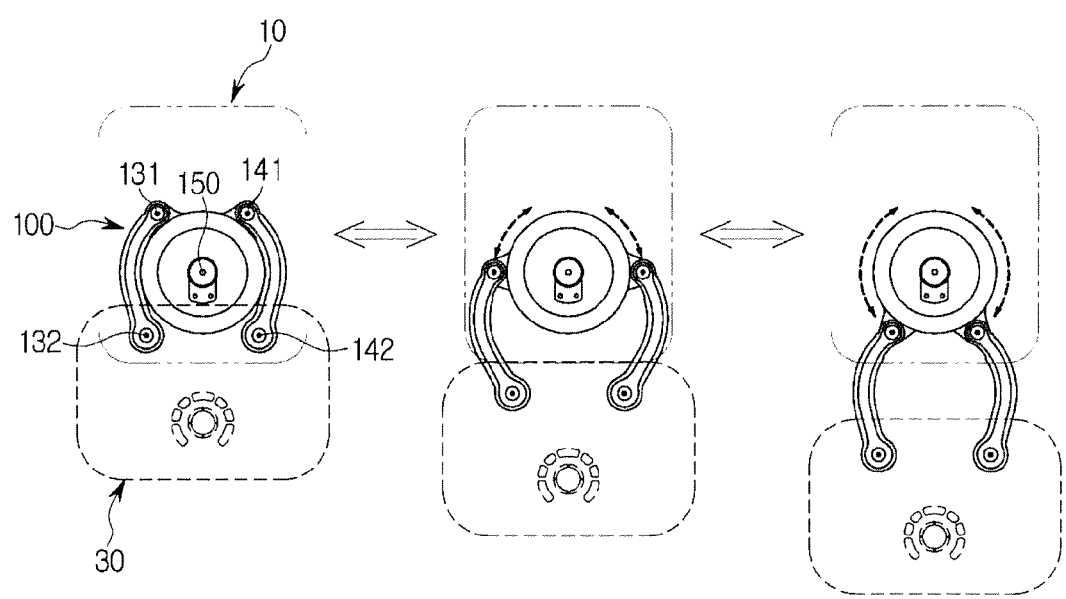
FIG. 6 is a view illustrating moving forward and backward of a mobile unit of the medical device of FIG. 1.

FIG. 6 is a view illustrating moving forward and backward of a mobile unit of the medical device of FIG. 1.

Referring to FIG. 6, the first hinge 131 and the second hinge 141 are placed in a rear limitation of the rotatable angle area, the first rotator 110 and the first connector 130 may be folded and the second rotator 120 and the second connector 140 may be folded. At this time, the control panel 30 may be mostly adjacent to the body 10, and this position may be defined as an initial position of the control panel 30.

When pulling the control panel 30 to the front side in the initial position of the control panel 30, the first rotator 110 and the first hinge 131 may be rotated counterclockwise about the rotation shaft 150, the second rotator 120 and the second hinge 141 may be rotated clockwise about the rotation shaft 150. When the first hinge 131 and the second hinge 141 reach a front limitation of the rotatable angle area, the control panel 30 may be placed in the furthest position from the body 10 in the front side.

During the control panel 30 is moved to the front side, the first connector 130 and the second connector 140 may be unfolded, and thus the first hinge 131 may be rotated clockwise about the first hinge pin 131a and the second hinge 141 may be rotated counterclockwise about the second hinge pin 141a.

In addition, during the control panel 30 is moved to the front side, the third hinge 132 may be rotated counterclockwise and then rotated clockwise, and the fourth hinge 142 may be rotated clockwise and then rotated counterclockwise.

Figure 7:
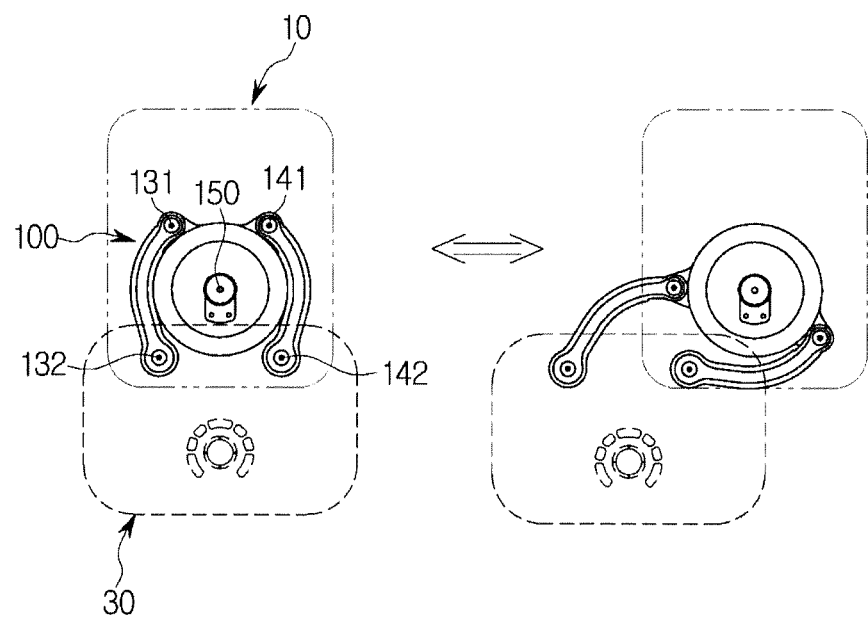
FIGS. 7 and 8 are views illustrating moving left side of a mobile unit of the medical device of FIG. 1.
Figure 8:
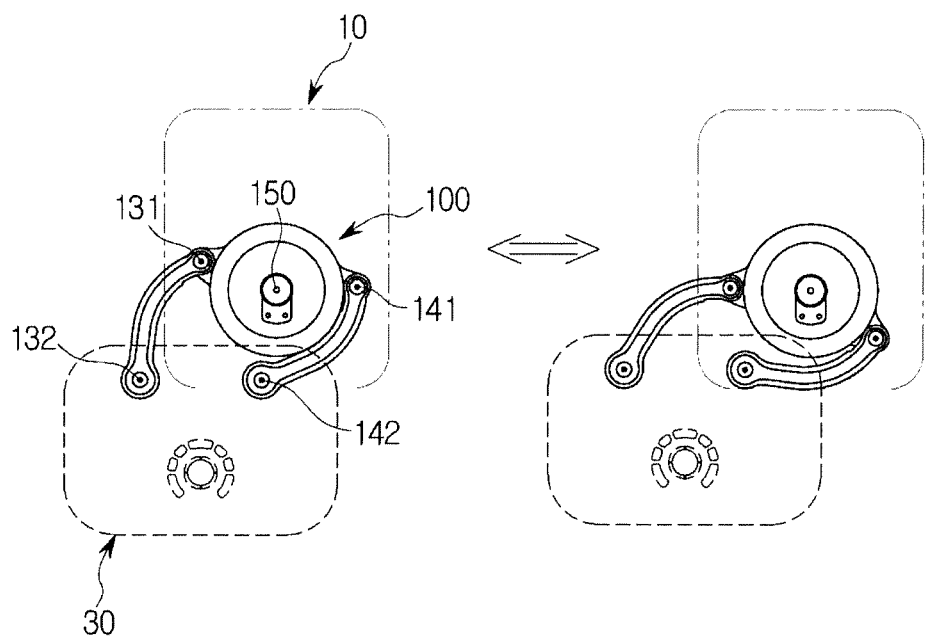

FIGS. 7 and 8 are views illustrating moving left side of a mobile unit of the medical device of FIG. 1.

Referring to FIG. 7, when pulling the control panel 30 from the initial position of the control panel 30 toward the left side, the first rotator 110 and the first hinge 131 may be rotated counterclockwise about the rotation shaft 150, the second rotator 120 and the second hinge 141 may be rotated clockwise about the rotation shaft 150.

In addition, since the second connector 140 is rotated while being unfolded and the first connector 130 is unfolded, only the first hinge 131 may be rotated clockwise about the first hinge pin 131a, and the second hinge 141 may be not rotated about the second hinge pin 141a. The third hinge 132 and the fourth hinge 142 may be rotated clockwise.

Referring to FIG. 8, when the first connector 130 is continuously moved to the left side, the first rotator 110 and the first hinge 131 may be continuously rotated counterclockwise about the rotation shaft 150, the second rotator 120 and the second hinge 141 may be continuously rotated clockwise about the rotation shaft 150, and when the second hinge 141 reaches the front limitation of the rotatable angel area, the control panel 30 may be placed in the furthest place from the body 10 in the left side.

Until the second hinge 141 reaches the front limitation of the rotatable angel area, the third hinge 132 and the fourth hinge 142 may be rotated clockwise about each hinge pin 132a and 142a. During this process, the first connector 130 may be continuously unfolded and the second connector 140 may be slightly unfolded, and thus the first hinge 131 may be rotated clockwise about the first hinge pin 131a and the second hinge 141 may be rotated counterclockwise about the second hinge pin 141a.

It may be possible that the control panel 30 returns to the initial position by pushing back to the right side.

Figure 9:
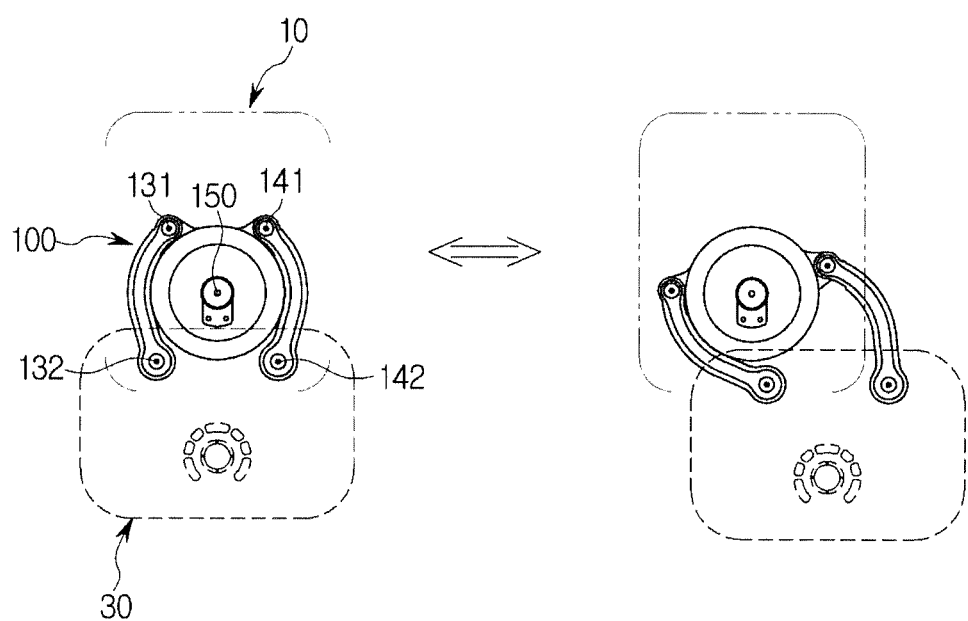
FIGS. 9 and 10 are views illustrating moving right side of a mobile unit of the medical device of FIG. 1.
Figure 10:
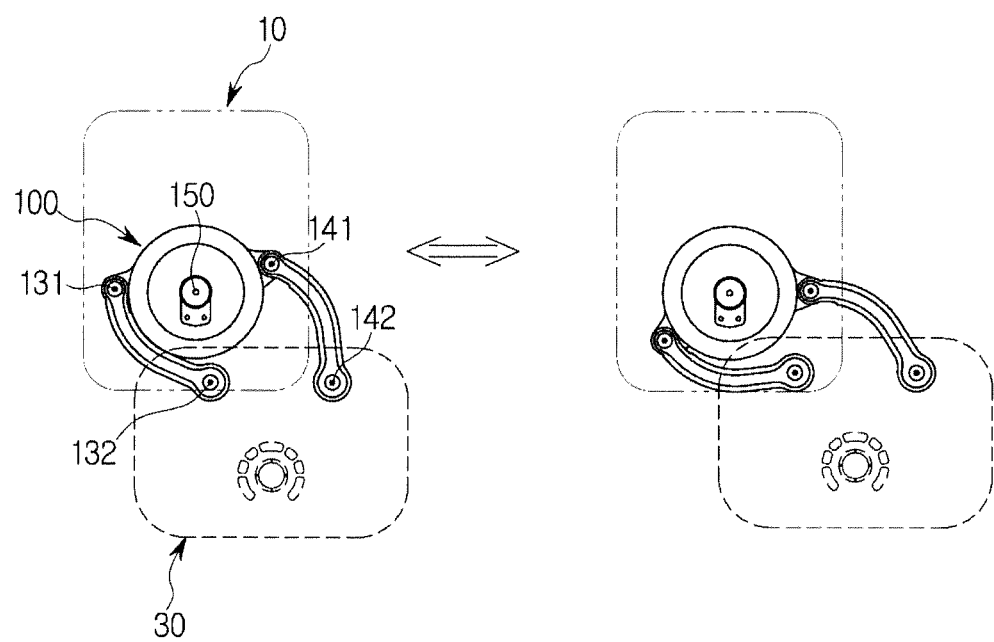

FIGS. 9 and 10 are views illustrating moving right side of a mobile unit of the medical device of FIG. 1.

Referring to FIG. 9, when pulling the control panel 30 from the initial position of the control panel 30 toward the right side, the first rotator 110 and the first hinge 131 may be rotated counterclockwise about the rotation shaft 150, and the second rotator 120 and the second hinge 141 may be rotated clockwise about the rotation shaft 150.

In addition, since the first connector 130 is rotated while being unfolded and the second connector 140 is unfolded, only the second hinge 141 may be rotated counterclockwise about the second hinge pin 141a, and the first hinge 131 may be not rotated about the first hinge pin 131a. The third hinge 132 and the fourth hinge 142 may be rotated counterclockwise about the hinge pin 132a and 142a, respectively.

Referring to FIG. 10, when the first connector 130 is continuously moved to the right side, the first rotator 110 and the first hinge 131 may be continuously rotated counterclockwise about the rotation shaft 150, and the second rotator 120 and the second hinge 141 may be continuously rotated clockwise about the rotation shaft 150, and when the first hinge 131 reaches the front limitation of the rotatable angel area, the control panel 30 may be placed in the furthest place from the body 10 in the right side.

Until the first hinge 131 reaches the front limitation of the rotatable angel area, the third hinge 132 and the fourth hinge 142 may be rotated counterclockwise about the hinge pin 132a and 142a, respectively. During this process, the second connector 140 may be continuously unfolded, and the first connector 130 may be slightly unfolded, and thus the first hinge 131 may be rotated clockwise about the first hinge pin 131a and the second hinge 141 may be rotated counterclockwise about the second hinge pin 141a.

It may be possible that the control panel 30 returns to the initial position by pushing back to the left side.

Meanwhile, the control panel 30 may be horizontally movable on a straight line at any position spaced apart from the body 10. Therefore, the efficiency of space utility may be improved, and the position of the control panel 30 may be easily regulated.

FIGS. 11 to 14 are views illustrating a random movement and a movement in a parabola in a horizontal plane of a mobile unit of the medical device of FIG. 1.

According to an embodiment of the present disclosure, in the connection device 100, the rotation of the first rotator 110 and the second rotator 120 and the rotation in each hinge may be integrally regulated, and thus the control panel 30 may be directly moved to any position on a horizontal plane, and the control panel 30 may be freely moved on any parabola or an arc on the horizontal plane.

Figure 11:
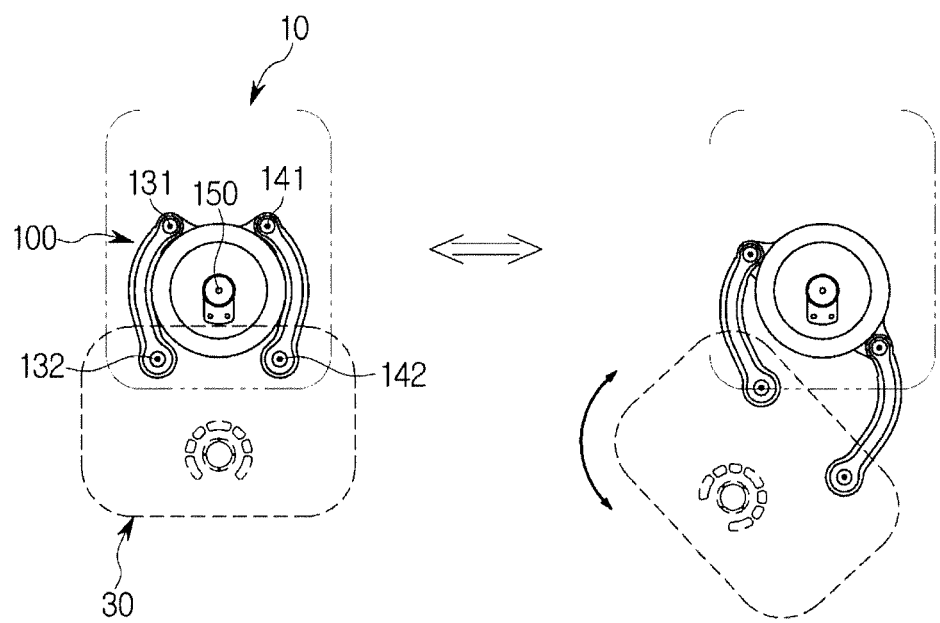
FIGS. 11 to 14 are views illustrating a random movement and a movement in a parabola in a horizontal plane of a mobile unit of the medical device of FIG. 1.

When a user in a 7 o'clock position is placed at a position facing the body 10, the user may immediately move the control panel 30 to the user's position by pulling the control panel 30 to the right side without a complicated operation, e.g. moving the body 10 or pulling the control panel 30 to the front side an then pulling it to the left side, as illustrated in FIG. 11.

Figure 12:
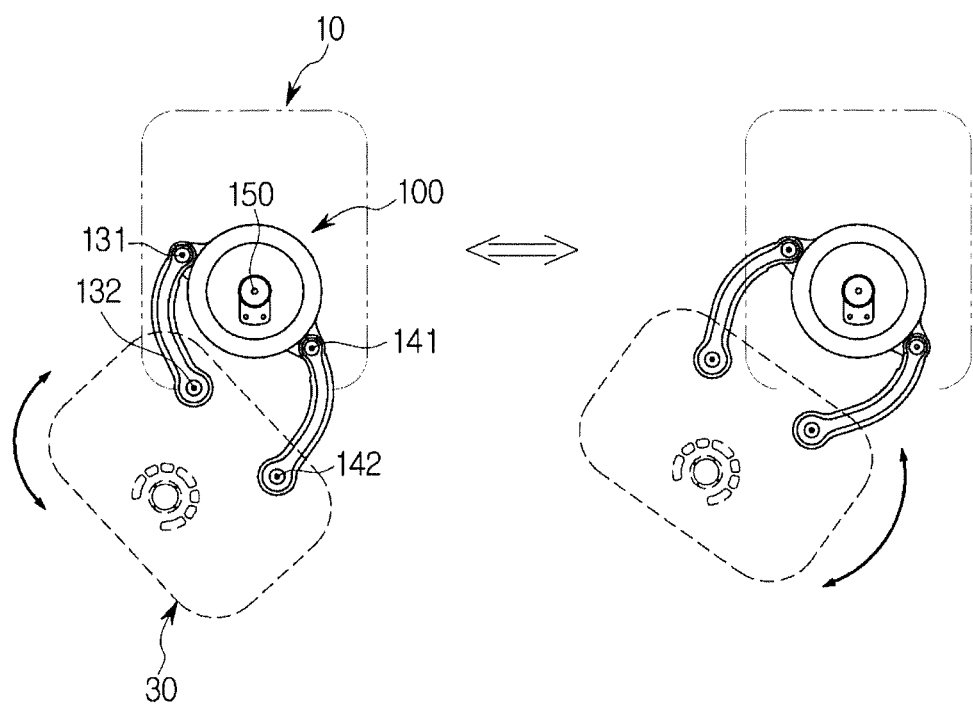

When the control panel 30 placed in a 7 o'clock position about the body 10 is needed to be moved counterclockwise, the user may push or pull the control panel 30 counterclockwise and then move the control panel 30 on the parabola or the arc, as illustrated in FIG. 12.

Figure 13:
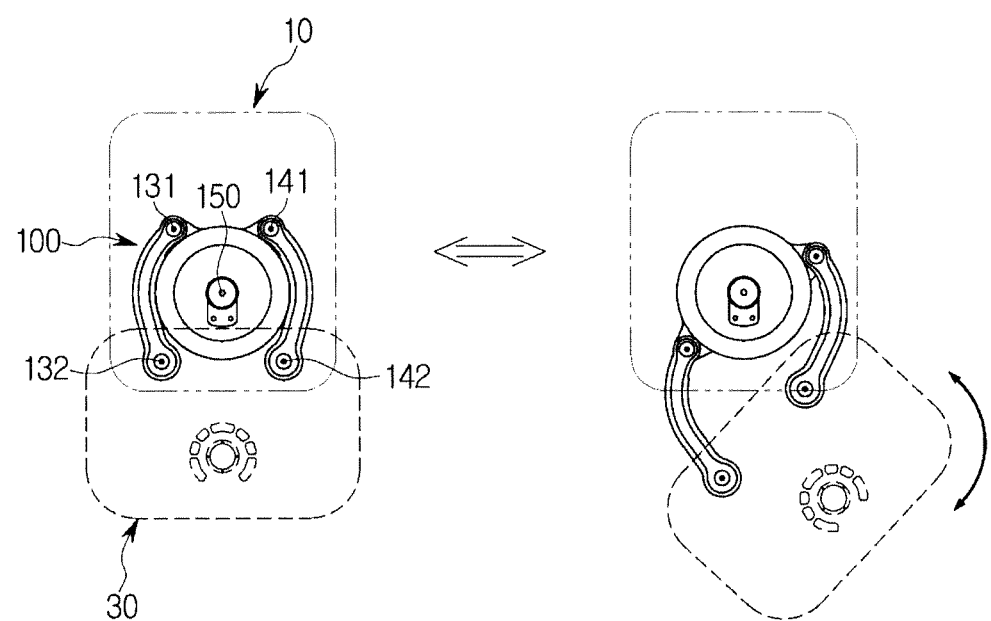

Meanwhile, when a user in a 5 o'clock position is placed at a position facing the body 10, the user may immediately move the control panel 30 to the user's position by pulling the control panel 30 in a 5 o'clock position without a complicated operation, e.g. moving the body 10 or pulling the control panel 30 to the front side an then pulling it to the right side, as illustrated in FIG. 13.

Figure 14:
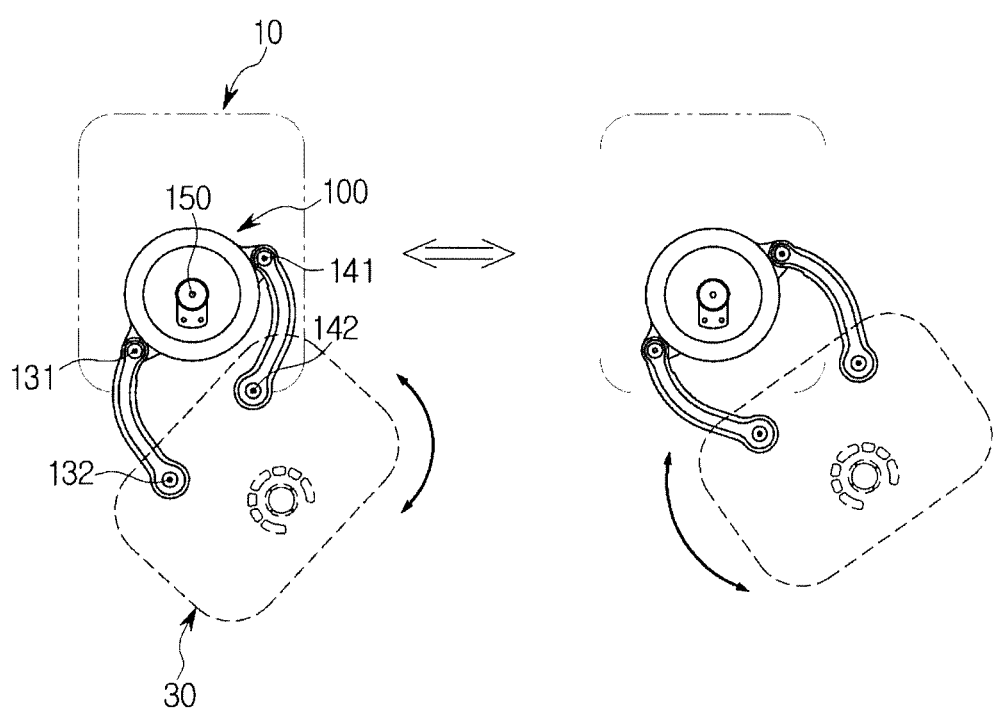

When the control panel 30 placed in a 5 o'clock position about the body 10 is needed to be moved clockwise, the user may push or pull the control panel 30 clockwise and then move the control panel 30 on the parabola or the arc, as illustrated in FIG. 14.

Figure 15:
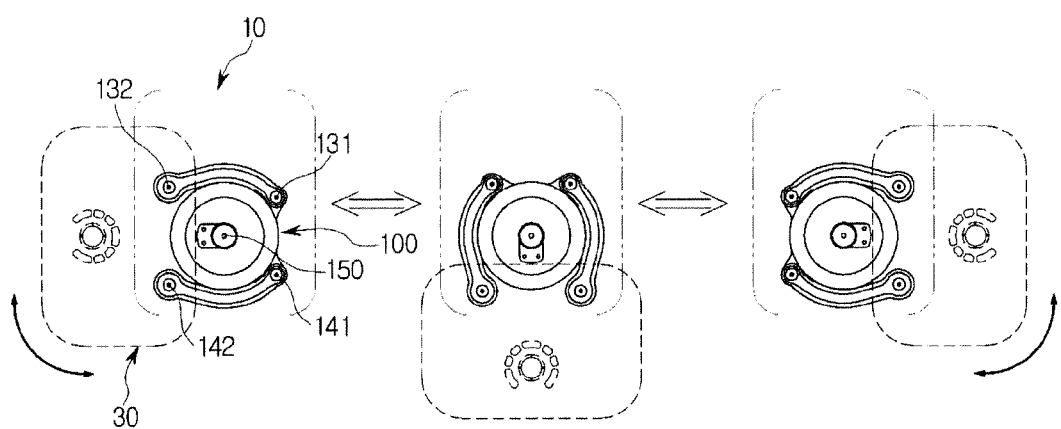
FIG. 15 is a view illustrating a rotary movement of the connection device of the medical device of FIG. 1.

FIG. 15 is a view illustrating a rotary movement of the connection device of the medical device of FIG. 1.

When the connection device 100 is non-rotatably mounted to the body 10, a movable area of the control panel 30 by the connection device 100 may be formed bilaterally symmetrical in the front side of the body 10, as illustrated in FIGS. 6 to 14.

Meanwhile, as illustrated in FIG. 15, when the connection device 100 is mounted to the body 10 to be pivoted, the initial position of the above-mentioned control panel 30 may be a position that is rotated about the body 10.

According to the user convenience, after rotating the initial position of the control panel 30 by rotating the connection device 100, the control panel 30 may be freely moved through the operation of components forming the connection device 100 of the control panel 30.

After moving the control panel 30 to a desired position, the position of the control panel 30 may be fixed. When a user uses the control panel 30 and when the control panel 30 is continuously moved by an external force while being not fixed, it may interrupt an examination. Therefore, the medical device according to an embodiment of the present disclosure may include a controller configured to control the movement of the control panel 30.

The controller may be mounted to a position that is needed for the fixation of the position of the control panel 30. For example, the controller may be mounted to at least one of the above-mentioned rotation shift 150 and the hinge 131, 132, 141, and 142 so that the rotators 110 and 120 and the connectors 130 and 140 connected to the hinge may be fixed to be not rotated. In addition, the controller may fix the connection device 100 so that the connection device 100 is fixed to prevent to pivot about the body 10 after rotating the initial position of the control panel 30.

The controller may be implemented by friction brake, electro-permanent magnet, and electromagnet, but is not limited thereto. Therefore, the controller may include any types as long as capable of fixing the control panel 30 to a certain position.

The input device provided in the control panel 30 may include a button configured to receive an input related to the fixation of the position of the control panel 30. When pressing the corresponding button, the input device transmits the received input to the controller such that the controller locks or unlocks the connection device 100. Thus, the control panel 30 may become a lock state or an unlock state.

For the user convenience, as mentioned above, the control panel 30 may be moved up and down that is the height of the control panel 30 may be adjusted as well as moved in the horizontal plane.

Therefore, the medical device according to an embodiment of the present disclosure may further include a lifting device disposed in a lower portion of the connection device 100 to move the control panel up and down.

The lifting device may be formed by well-known technology, and the input device provided in the control panel 30 may include a button receiving an input of a command related to adjusting the height of the control panel 30. The user may move the control panel 30 to an upper side or a lower side by operating the input device.

Hereinafter in a medical device according to another embodiment of the present disclosure, a structure of connectors configured to connect a control panel 30 to a body 10, and an operation of the control panel 30 performed through the structure will be described.

Figure 16:
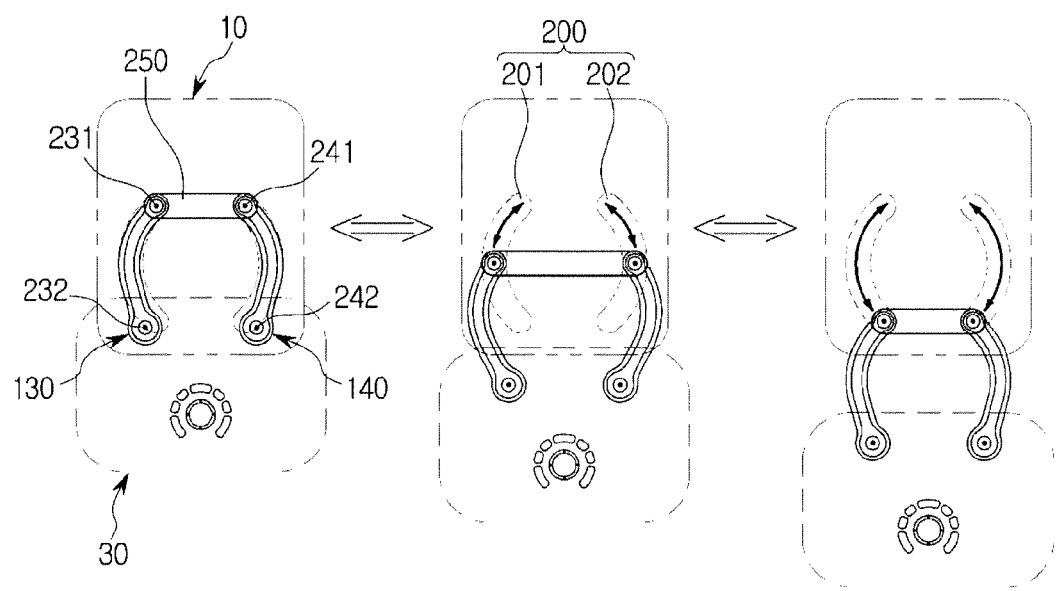
FIG. 16 is a view illustrating moving forward and backward of a mobile unit of a medical device according to another embodiment of the present disclosure.
Figure 17:
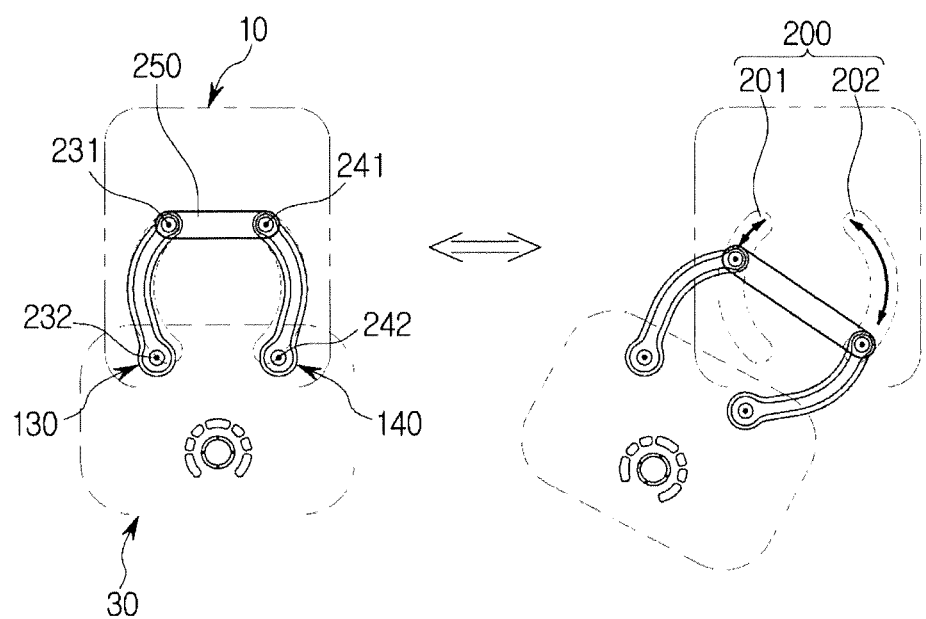
FIGS. 17 and 18 are views illustrating a random movement and a movement in a parabola in a horizontal plane of a mobile unit of the medical device of FIG. 16.
Figure 18:
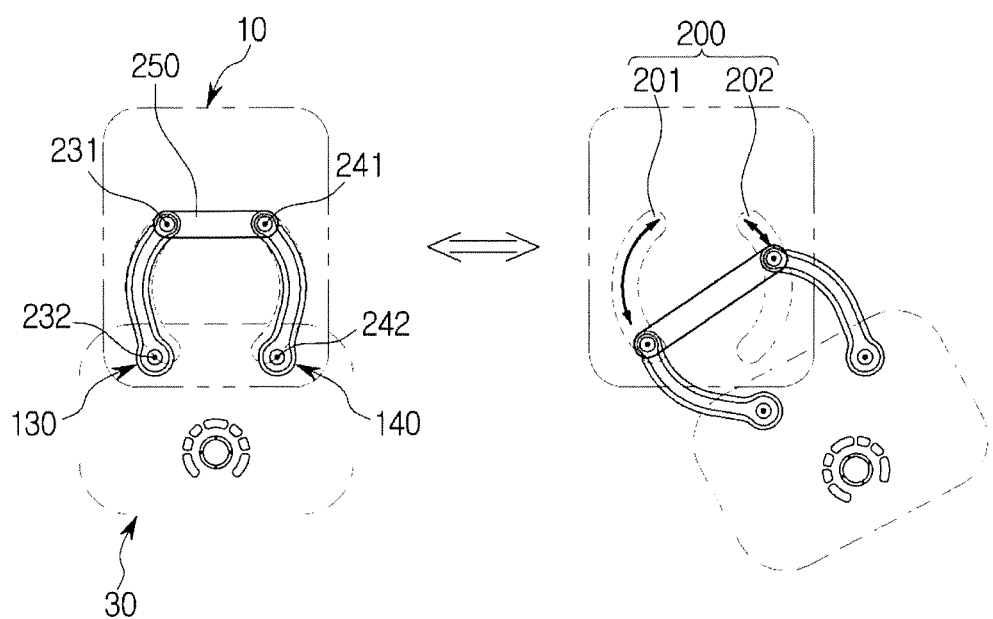

FIG. 16 is a view illustrating moving forward and backward of a mobile unit of a medical device according to another embodiment of the present disclosure and FIGS. 17 and 18 are views illustrating a random movement of a mobile unit of the medical device of FIG. 16 in a horizontal plane and a parabola.

Referring to FIGS. 16 to 18, a medical device may include a first connector 130 and a second connector 140 both of which are configured to connect a body 10 to a control panel 30. In addition, the first connector 130 may include a first connection part 231 rotatably coupled to the body 10, and a second connection part 232 rotatably coupled to a mobile unit 30. In addition, the second connector 140 may include a third connection part 241 rotatably coupled to the body 10 and a fourth connection part 242 rotatably coupled to the mobile unit 30.

At least one of the body 10 and the control panel 30 may include a guide rail 200. The guide rail 200 may be integrally formed with the body 10 or the control panel 30. At least one of the first connection part 231 and the second connection part 232 of the first connector 130 may be moved along the guide rail 200 in a slide manner. In addition, at least one of the third connection part 241 and the fourth connection part 242 of the second connector 140 may be moved along the guide rail 200 in a slide manner. According to an embodiment of the present disclosure, the guide rail 200 may be formed on an upper side of the body 10 or a lower side of the control panel 30.

As illustrated in FIGS. 16 to 18, when the guide rail 200 is formed in the body 10, the first connection part 231 of the first connector 130 and the third connection part 241 of the second connector 140 may be moved along the guide rail 200 in a slide manner.

Although not shown in the drawings, when the guide rail 200 is formed in a lower surface of the control panel 30, the second connection part 232 of the first connector 130 and the fourth connection part 242 of the second connector 140 may be moved along the guide rail 200 in the slide manner.

In addition, the medical device may include a link 250 having a variable length and configured to connect the first connection part 231 and the third connection part 241 and/or the second connection part 232 and the fourth connection part 242 moved in the slide manner. Through the link 250 connecting the first connector 130 to the second connector 140, an external force of the user for the movement of the control panel 30 may be evenly distributed in the first connector 130 and the second connector 140, and accordingly the control panel 30 may be more easily moved.

The guide rail 200 may include a first rail 201 in which the first connection part 231 or the second connection part 232 of the first connector 130 is moved in the slide manner and a second rail 202 in which the third connection part 241 or the fourth connection part 242 of the second connector 140 is moved in the slide manner. In addition, the first rail 201 and the second rail 202 may formed in an arc shape, wherein the arc shape of the first rail 201 and the second rail 202 may have the same radius of curvature, and the same center of curvature, and may be bilaterally symmetrical.

In addition, the first connector 130 and the second connector 140 may have a curved shape to correspond to the guide rail 200 having the arc shape. When the first connector 130 and the second connector 140 have a curved shape to correspond to the shape of the first rail 201 and the second rail 202, a direction of a force, which is applied to the first connection part 231 and the third connection part 241 and/or the second connection part 232 and the fourth connection part 242 moved along the guide rail 200 in the slide manner, through the first connector 130 and the second connector 140 may be coincided with the direction of the first rail 201 and the second rail 202 and thus it may be advantageous to deliver the force. Therefore, the user may move the control panel 30 easier.

Referring to FIG. 16, the first connection part 231 and the third connection part 241 moved along the guide rail 200 in the slide manner are placed in a rear limitation of the guide rail 200, the control panel 30 may be placed in the closest position to the body 10, and this position may be defined as an initial position of the control panel 30.

When pulling the control panel 30 to the front side from the initial position of the control panel 30, the first connection part 231 and the third connection part 241 may be moved to the front side along the guide rail 200. When the first connection part 231 and the third connection part 241 reach the front limitation of the guide rail 200, the control panel 30 may be placed in the furthest position from the body 10 in the front side.

During the control panel 30 is moved to the front side, the first connection part 231 may be rotated clockwise about a shaft of the first connection part 231, and the third connection part 241 may be rotated counterclockwise about a shaft of the third connection part 241.

In addition, during the control panel 30 is moved to the front side, the second connection part 232 may be rotated counterclockwise and then rotated clockwise, and the fourth connection part 242 may be rotated clockwise and then rotated counterclockwise.

Referring to FIGS. 17 and 18, the movement of the first connection part 231 and the third connection part 241 and the rotation in each connection part may be integrally regulated, and thus the control panel 30 may be directly moved to any position on a horizontal plane, and the control panel 30 may be freely moved on any parabola or an arc on the horizontal plane.

When a user in a 7 o'clock position is placed at a position facing the body 10, the user may immediately move the control panel 30 to the user's position by pulling the control panel 30 to the right side without a complicated operation, e.g. moving the body 10 or pulling the control panel 30 to the front side an then pulling it to the left side, as illustrated in FIG. 17.

When the control panel 30 placed in a 7 o'clock position about the body 10 is needed to be moved counterclockwise, the user may move the control panel 30 on the parabola or the arc by pushing or pulling the control panel 30 counterclockwise.

Meanwhile, when a user in a 5 o'clock position is placed at a position facing the body 10, the user may immediately move the control panel 30 to the user's position by pulling the control panel 30 in a 5 o'clock position without a complicated operation, e.g. moving the body 10 or pulling the control panel 30 to the front side an then pulling it to the right side, as illustrated in FIG. 18.

When the control panel 30 placed in a 5 o'clock position about the body 10 is needed to be moved clockwise, the user may move the control panel 30 on the parabola or the arc by pushing or pulling the control panel 30 clockwise.

It may be possible that the control panel 30 returns to the initial position by being pulled or being pushed again to a front, back, left, and right side.

When the guide rail 200 is not allowed to pivot since the guide rail 200 is fixed to the body 10 or the control panel 30, the movable area of the control panel 30 may be formed bilaterally symmetrical in the front side of the body 10.

Meanwhile, the guide rail 200 may be installed in a base coupled to the body 10 or the control panel 30.

Hereinafter in a medical device according to another embodiment of the present, in which a guide rail is installed in a base coupled a body 10 or a control panel 30, a structure of connectors connecting the control panel 30 to the body 10, and an operation of the control panel 30 performed by the structure may be described in detail.

Figure 19:
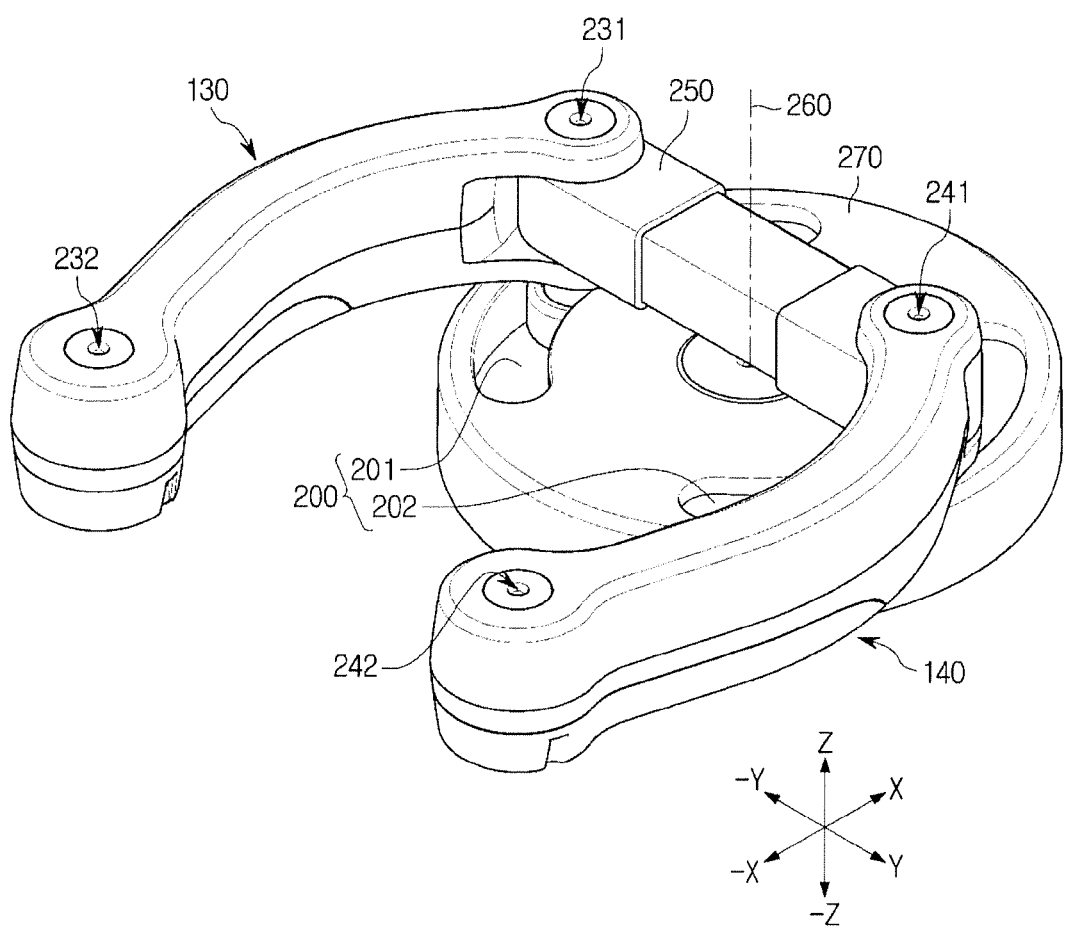
FIG. 19 is a perspective view illustrating of a connection device of a medical device according to another embodiment of the present disclosure.
Figure 20:
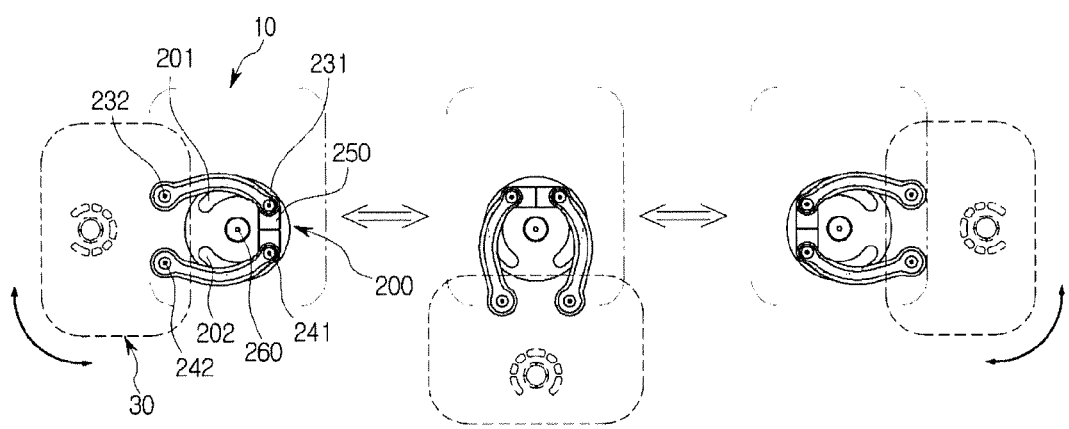
FIG. 20 is a view illustrating a rotary movement of the connection device of the medical device of FIG. 19.

FIG. 19 is a perspective view illustrating of a connection device of a medical device according to another embodiment of the present disclosure and FIG. 20 is a view illustrating a rotary movement of the connection device of the medical device of FIG. 19.

Another component in an embodiment of the present disclosure illustrated in FIGS. 19 and 20, except that the guide rail 200 is installed in the base 270, may be the same as those in an embodiment of the present disclosure illustrated in FIGS. 16 to 18. Accordingly, a description of the same component will be omitted.

Referring to FIG. 19, the base 270 may be rotatably coupled to the body 10 or the control panel 30 about a rotation shaft 260. The base 270 may be formed in approximately disk shape having a certain thickness, and the guide rail 200 may be formed on an upper surface of the base 270.

Although not shown in the drawings, the guide rail 200 may be formed in a lateral side of the base 270.

Referring to FIG. 20, the base 270 in which the guide rail 200 is installed may be rotatable about the body 10 or the control panel 30 so that an initial position of the control panel 30 may be a rotated position about the body 10.

According to the user convenience, after rotating the initial position of the control panel 30 by rotating the base 270, the control panel 30 may be freely moved by an operation of connectors 130 and 140.

Hereinafter another embodiment in which the guide rail 200 is installed in a base coupled to the body 10 or the control panel 30 will be described.

Figure 21:
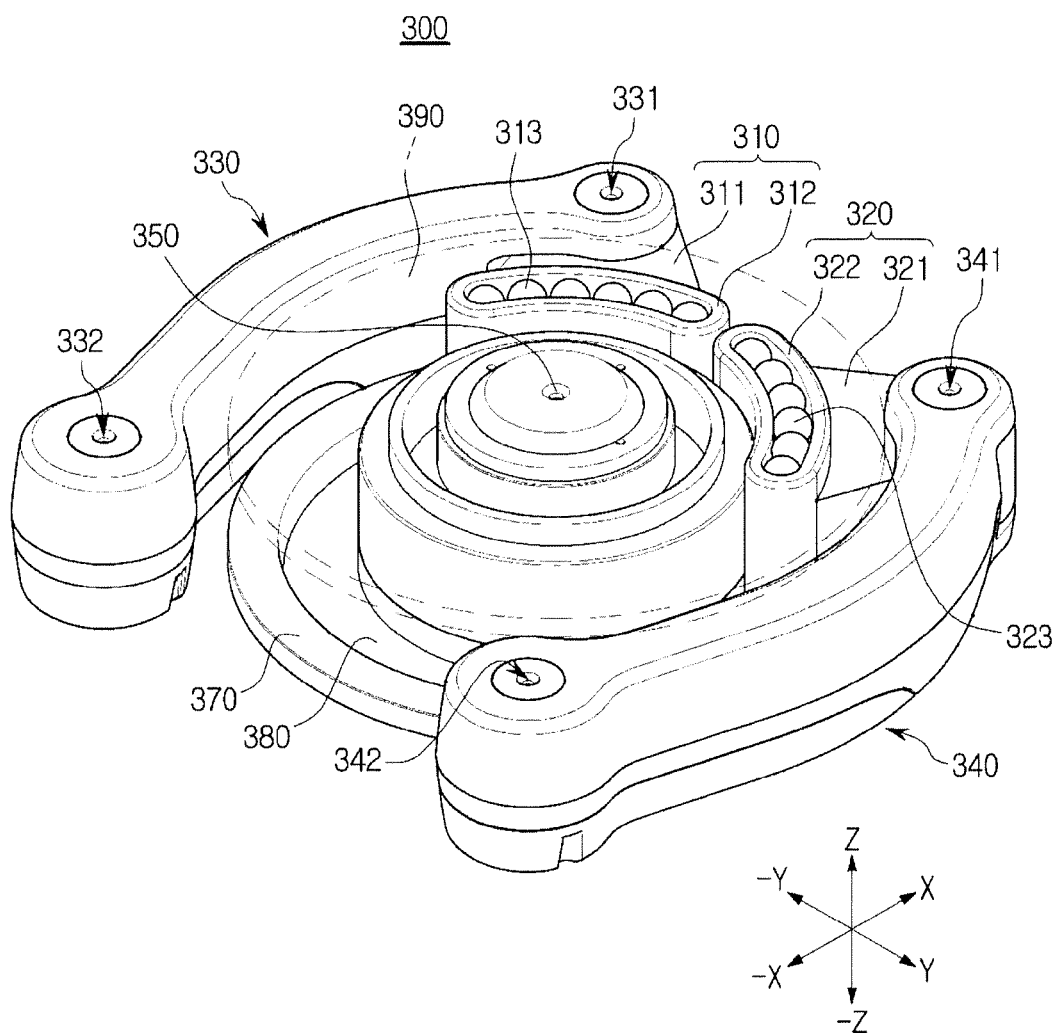
FIG. 21 is a perspective view illustrating of a connection device of a medical device according to another embodiment of the present disclosure.
Figure 22:
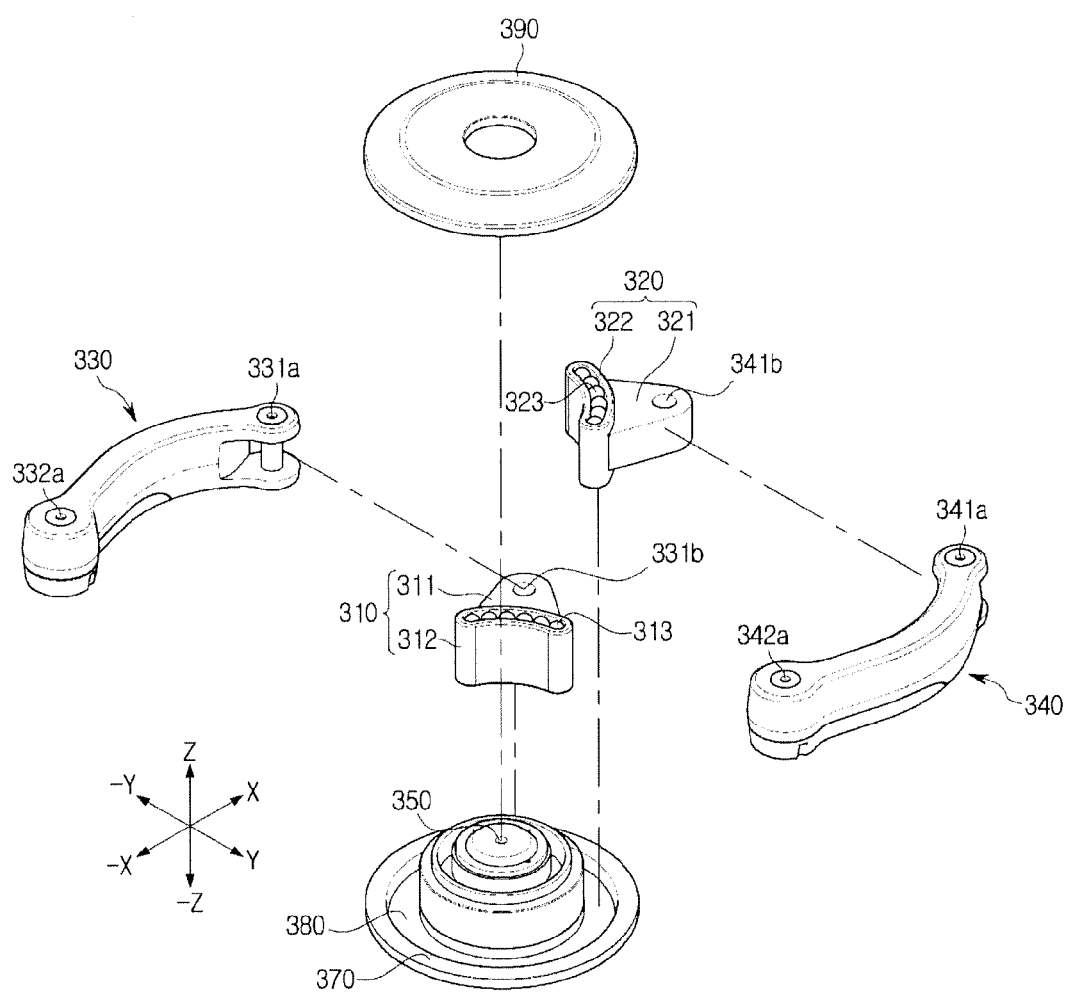
FIG. 22 is an exploded perspective view illustrating the connection device of the medical device of FIG. 21.

FIG. 21 is a perspective view illustrating of a connection device of a medical device according to another embodiment of the present disclosure and FIG. 22 is an exploded perspective view illustrating the connection device of the medical device of FIG. 21.

Referring to FIGS. 21 and 22, a connection device 300 of a medical device according to another embodiment of the present disclosure may include a base 370 coupled to a body 10 or a control panel 30, wherein a guide rail 380 may be installed in the base 370.

The base 370 may be formed in any shape, but may be formed in approximately disk shape about a shaft 350. In addition, the guide rail 380 may have a circular shape having the same a center of curvature as the base 370.

In addition, the connection device 300 may include a first rotator 310 and a second rotator 320 both of which are moved in the guide rail 380 in the slide manner, and may include a first connector 330 pivotally connected to the first rotator 310 and a second connector 340 pivotally connected to the second rotator 320.

Although not shown in the drawings, the guide rail 380 may include a first rail in which the first rotator 310 is moved in the slide manner and a second rail in which the second rotator 320 is moved in the slide manner. In addition, the first rail and the second rail may formed in an arc shape having the same radius of curvature, and the same center of curvature, and being bilaterally symmetrical.

The first rotator 310 and the second rotator 320 may include a first rotation part 312 and a second rotation part 322 both of which are accommodated and rotated in the guide rail 380, respectively. The rotation part 311 and 321 may be formed in an arc shape to be accommodated and rotated in the guide rail 380. In addition, the rotation part 312 and 322 may include bearing ball 313 and 323 to be smoothly moved in the guide rail 380.

The first connector 330 may include a first connector 331 rotatably connected the first rotator 310, and a second connector 332 rotatably connected to the body 10 or the control panel 30 that is not coupled to the base 370.

The second connector 340 may include a first connector 341 rotatably connected the second rotator 320, and a second connector 342 rotatably connected to the body 10 or the control panel 30 that is not coupled to the base 370.

Each hinge pin 331a, 332a, 341a, and 342a may be provided in each connection part 331, 332, 341 and 342.

The first rotator 310 and the second rotator 320 may include a first hinge 311 connected to the first connector 330 and a second hinge 321 connected to the second connector 340. The first hinge 311 and the second hinge 321 may extend to a lateral side from the first rotation part 312 and the second rotation part 322, respectively, and a first hinge hole 331b and a second hinge hole 341b both of which are connected to the 331a and the 341a may be provided in an end portion of each hinge 311 and 321.

The connection device 300 may include a cover 390 covering an upper surface of the base 370 in which the first rotator 310 and the second rotator 320 are accommodated. On a lower surface of the cover 390, a rail may be formed to accommodate the rotation part 312 and 322 of the rotator 310 and 320 to correspond to the guide rail 380 installed in the base 370.

Figure 23:
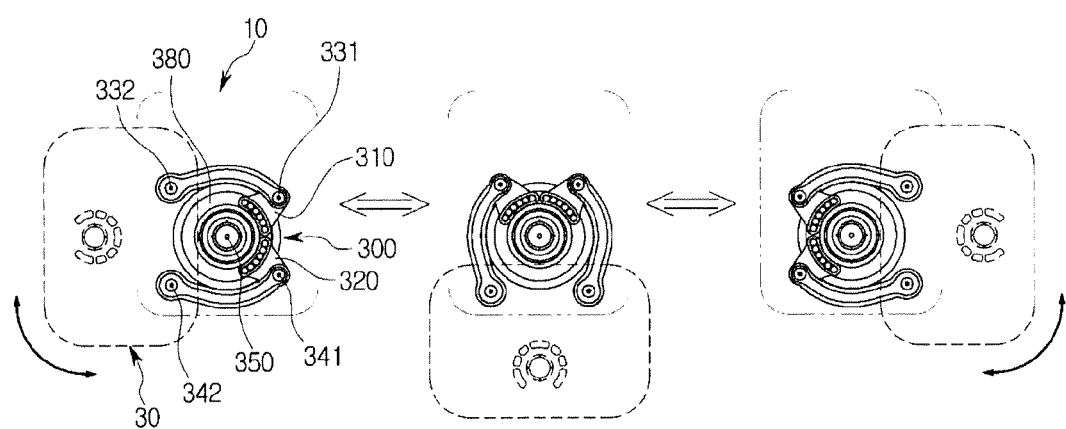
FIG. 23 is a view illustrating a rotary movement of the connection device of the medical device of FIG. 21.

FIG. 23 is a view illustrating a rotary movement of the connection device of the medical device of FIG. 21.

As illustrated in FIG. 23, when the guide rail 380 is formed in the circular shape, even if the base 370 is not rotatably coupled to the body 10 or the control panel 30, the first rotator 310 and the second rotator 320 may be moved along the guide rail 380 so that the control panel 30 may be rotated against the body 10 about the shaft 350 of the base 370.

Although not shown in the drawings, when the guide rail 380 is configured with the first rail and the second rail formed in the arc shape having the same radius of curvature, and the same center of curvature, and being bilaterally symmetrical, there may be a limitation in an angle in which the first rotator 310 and the second rotator 320 are movable and thus the control panel 30 may be not allowed to be rotated, as illustrated in FIG. 23.

Therefore, in a state in which the guide rail 380 is configured with the first rail and the second rail, when the base 370 is coupled to the body 10 or the control panel 30 to be rotatable about the rotation shaft 350, the initial position of the control panel 30 may be a rotated position against the body 10, as illustrated in FIG. 23.

As is apparent from the above description, according to the proposed medical device, the control panel may be freely moved to the user desired position and thus the user convenience may be enhanced. In addition, the efficiency of space utility may be improved since moving the control panel to the user desired position is performed without a movement passing through an unnecessary position.

Hereinbefore in an ultrasonic diagnosis apparatus as an example of a medical device, a movement of a control panel is described as an example of a mobile unit included in the ultrasonic diagnosis apparatus. Therefore, it may be understood that as well as a control panel, another mobile unit, e.g. a display may be moved as mentioned above, and in addition, a mobile unit included in another medical device, as well as an ultrasonic diagnosis apparatus may be moved as mentioned above.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A medical device comprising:
a body;
a mobile unit movably connected to the body; and
a connection device configured to provide a movable connection between the body and the mobile unit, wherein the connection device comprises a first rotator and a second rotator, both of which are rotatably connected to the body at a common axis and configured to rotate about the common axis; a first connector pivotally connected to the first rotator; and a second connector pivotally connected to the second rotator.

2. The medical device of claim 1, wherein:
the first connector and the second connector are pivotally connected to the mobile unit.

3. The medical device of claim 2, wherein:
the first rotator and the second rotator have a disk shape having the same radius, and
the first connector is pivotally connected an outer circumference of the first rotator and the second connector is pivotally connected an outer circumference of the second rotator.

4. The medical device of claim 3, wherein:
the first connector and the second connector have a curved shape to surround the outer circumferences of the first rotator and the second rotator.

5. The medical device of claim 3, wherein
the connection device further comprises a rotation control member configured to limit a rotation angle of the first rotator and the second rotator, and
a rotatable angle area of a first hinge, in which the first rotator and the first connector are connected to each other, and a second hinge, in which the second rotator and the second connector are connected to each other, are limited through the rotation control member.

6. The medical device of claim 5, wherein:
a rotatable angle area of the first rotator and the second rotator, which is limited by the rotation control member, is bilaterally symmetrical about a rotation shaft.

7. The medical device of claim 1, wherein:
the connection device further comprises a first controller configured to control a rotation of the first rotator and the second rotator.

8. The medical device of claim 7, wherein
the connection device further comprises a second controller configured to control a pivot of the first connector and the second connector.

9. The medical device of claim 1, wherein
the first rotator and the second rotator are rotatably connected to the mobile unit, and the first connector and the second connector are rotatably connected to the body.

10. A medical device comprising:
a body;
a mobile unit movably connected to the body; and
a connection device configured to provide a movable connection between the body and the mobile unit, wherein the connection device comprises a first hinge and a second hinge both of which are connected to and rotated about a common rotation shaft having a common axis and configured to rotate about the common axis; a third hinge rotated about the first hinge; and a fourth hinge rotated about the second hinge.

11. The medical device of claim 10, wherein:
the rotation shaft is connected to the body, and the third hinge and the fourth hinge are connected to the mobile unit.

12. The medical device of claim 10, wherein:
the connection device further comprises a rotation control member configured to limit a rotation angle of the first hinge and the second hinge.

13. The medical device of claim 12, wherein:
the first hinge and the second hinge have the same rotation radius, and
a rotatable angle area of the first hinge and the second hinge is bilaterally symmetrical about the rotation shaft.

14. The medical device of claim 10, wherein:
the connection device further comprises a first controller configured to control a rotation of the first hinge and the second hinge about the rotation shaft.

15. The medical device of claim 14, wherein:
the connection device further comprises a second controller configured to control a rotation of one or more of the first hinge and the third hinge, and one or more of the second hinge and the fourth hinge.

16. The medical device of claim 10, wherein:
the rotation shaft is connected to the mobile unit, and the third hinge and the fourth hinge are connected to the body.

17. A medical device comprising:
a body;
a mobile unit movably connected to the body; and
a connection device configured to provide a movable connection between the body and the mobile unit,
wherein the connection device comprises a first rotator and a second rotator both of which are rotatably coupled to a rotation shaft, which is provided in a base, and having a disk shape having the same radius; a first connector whose one end portion is pivotally connected to an outer circumference of the first rotator; and a second connector whose one end portion is pivotally connected to an outer circumference of the second rotator.

18. The medical device of claim 17, wherein:
the base is fixed to the body, and the other end portion of the first connector and the other end portion of the second connector are pivotally connected to the mobile unit.

19. The medical device of claim 17, wherein:
the connection device further comprises a rotation control member configured to limit a rotation angle of the first rotator and the second rotator,
the rotation control member is positioned spaced apart from the rotation shaft with a certain distance to have a pillar shape so as to penetrate the first rotator and the second rotator, and
the first rotator and the second rotator respectively comprise a guide slit formed in an arc shape to guide a rotation area limited by the rotation control member and to allow the rotation control member to penetrate thereto.

20. The medical device of claim 19, wherein:
the connection device further comprises a cap non-rotatably coupled to the other end of the rotation shaft whose one end is fixed to a base, and
opposite ends of the rotation control member are fixed to the base and the cap, respectively.

21. The medical device of claim 20, wherein:
the guide slit of the first rotator and the guide slit of the second rotator are symmetric about the rotation shaft so that rotatable angle areas of the first rotator and the second rotator are symmetrical about the rotation shaft.

22. The medical device of claim 17, wherein:
the first connector and the second connector have a curved shape in a state of being folded so as to surround an outer circumference of the first rotator and the second rotator.

23. The medical device of claim 17, wherein:
the connection device further comprises a first controller configured to control a rotation of the first rotator and the second rotator, and a second controller configured to control a pivot of the first connector and the second connector.

24. The medical device of claim 17, wherein:
the base is rotatably fixed to the body or the mobile unit so that the connection device is pivoted against the body.

25. The medical device of claim 24, further comprising:
a controller configured to control a rotation of the base.

26. The medical device of claim 17, further comprising:
a lifting device disposed between the base and the body to move the mobile unit up and down.

27. The medical device of claim 17, wherein:
the based is fixed to the mobile unit, and the other end portion of the first connector and the other end portion of the second connector are pivotally connected to the body.

28. A medical device comprising:
a body;
a mobile unit; and
a connection device connecting the body and the mobile unit to each other, and including a first connector having first and third ends respectively connected to the body and the mobile unit and rotatable around each other, and a second connector having second and fourth ends respectively connected to the body and the mobile unit and rotatable around each other,
wherein two ends selected from a first pair of ends including the first end of the first connector and the second end of the second connector and a second pair of ends including the third end of the first connector and the fourth end of the second connector, are respectively rotatable along first and second concentric paths in one of the body and mobile unit, and
the other two ends selected from the first and second pairs are pivotally connected to the other one of the body and mobile unit.

29. The medical device of claim 28, further comprising:
a rotation shaft; and
first and second rotators rotatable around the rotation shaft, centers of the first and second rotators penetrated by the rotation shaft,
wherein the first end of the first connector is connected to an edge of the first rotator and the second end of the second connector is connected to an edge of the second rotator.

30. The medical device of claim 28, wherein:
the first and second concentric paths are respectively determined by first and second guide rails in the one of the body and mobile unit, and
the first end of the first connector and the second end of the second connector are connected by a length adjustable link, and are slidable along the first and second guide rails, respectively.

31. The medical device of claim 28, further comprising a base including first and second guide rails and rotatable around a rotation shaft located at a center of the base,
wherein the first end of the first connector and the second end of the second connector are connected by a length adjustable link, and are slidable along the first and second guide rails, respectively.

32. The medical device of claim 28, further comprising a base including first and second guide rails,
wherein the first end of the first connector and the second end of the second connector are respectively coupled to the first and second guide rails by first and second bearings which are slidable in the first and second guide rails.

* * * * *